(12) United States Patent
Nyhart, Jr.

(10) Patent No.: US 6,985,770 B2
(45) Date of Patent: Jan. 10, 2006

(54) APPARATUS FOR THE CONTROLLABLE MODIFICATION OF COMPOUND CONCENTRATION IN A TUBE

(75) Inventor: Eldon H. Nyhart, Jr., Zionsville, IN (US)

(73) Assignee: Biosynergetics, Inc., Zionsville, IN (US)

( * ) Notice: Subject to any disclaimer, the term of this patent is extended or adjusted under 35 U.S.C. 154(b) by 791 days.

(21) Appl. No.: 10/039,797

(22) Filed: Oct. 26, 2001

(65) Prior Publication Data

US 2002/0065493 A1  May 30, 2002

Related U.S. Application Data

(62) Division of application No. 09/692,857, filed on Oct. 20, 2000, now Pat. No. 6,738,661.
(60) Provisional application No. 60/170,051, filed on Dec. 10, 1999, and provisional application No. 60/161,130, filed on Oct. 22, 1999.

(51) Int. Cl.
*A61N 1/30* (2006.01)

(52) U.S. Cl. ...................................... 604/20
(58) Field of Classification Search ............. 604/20–21, 604/264, 266, 65–67; 606/27, 32–33, 2, 10, 606/13, 14; 424/422–423
See application file for complete search history.

(56) References Cited

U.S. PATENT DOCUMENTS

| | | | |
|---|---|---|---|
| 2,883,986 A | 4/1959 | De Luca et al. | |
| 3,435,826 A | 4/1969 | Fogarty | |
| 3,467,101 A | 9/1969 | Fogarty et al. | |
| 3,570,476 A | 3/1971 | Gregg | |
| 3,901,829 A | 8/1975 | Slingluff et al. | |
| 4,062,746 A | 12/1977 | Rich et al. | |
| 4,156,066 A | 5/1979 | Gould | |
| 4,156,067 A | 5/1979 | Gould | |
| 4,195,637 A | 4/1980 | Gruntzig et al. | |
| 4,271,839 A | 6/1981 | Fogarty et al. | |
| 4,289,128 A | 9/1981 | Rusch | |
| 4,323,071 A | 4/1982 | Simpson et al. | |
| 4,359,453 A | 11/1982 | Gordon | |
| 4,403,984 A | 9/1983 | Ash et al. | |

(Continued)

FOREIGN PATENT DOCUMENTS

| | | |
|---|---|---|
| WO | WO 91/19452 | 12/1991 |
| WO | WO 93/14807 | 8/1993 |
| WO | WO 98/50095 | 11/1998 |
| WO | WO 00/67820 | 11/2000 |
| WO | WO 02/094099 A1 | 11/2002 |

OTHER PUBLICATIONS

Voss, Richard F., *Fractals in nature: From characterization to simulation*, The Science of Fractional Images, (1988) Chapter 1, pp. 39–70, Springer–Verlag, New York.

*Primary Examiner*—LoAn H. Thanh
(74) *Attorney, Agent, or Firm*—Woodard, Emhardt, Moriarty, McNett & Henry LLP

(57) ABSTRACT

Apparatus and methods for delivery of a drug or compound into a fluid flowing within a tube or catheter. In one embodiment a catheter includes an inner surface and polymer matrix such as a hydrogel. The hydrogel includes captured within it a therapeutic agent. The method of capture may be by various means, including photolabile bonds between the therapeutic agent and the hydrogel. The therapeutic agent is released from the hydrogel by the application of energy to the hydrogel, such as by a laser emitting a wavelength which resonates and breaks the photolabile bond. The released therapeutic agent diffuses out of the hydrogel into the liquid flowing within a lumen of the catheter.

15 Claims, 14 Drawing Sheets

U.S. PATENT DOCUMENTS

| | | | |
|---|---|---|---|
| 4,479,497 A | 10/1984 | Fogarty et al. | |
| 4,531,943 A | 7/1985 | Van Tassel et al. | |
| 4,545,390 A | 10/1985 | Leary | |
| 4,554,929 A | 11/1985 | Samson et al. | |
| 4,571,240 A | 2/1986 | Samson et al. | |
| 4,573,966 A | 3/1986 | Weikl et al. | |
| 4,581,017 A | 4/1986 | Sahota | |
| 4,582,181 A | 4/1986 | Samson | |
| 4,597,755 A | 7/1986 | Samson et al. | |
| 4,610,241 A | 9/1986 | Gordon | |
| 4,616,648 A | 10/1986 | Simpson | |
| 4,702,252 A | 10/1987 | Brooks et al. | |
| 4,741,732 A | 5/1988 | Crankshaw et al. | |
| 4,743,673 A | 5/1988 | Johnston et al. | |
| 4,748,982 A | 6/1988 | Horzewski et al. | |
| 4,762,129 A | 8/1988 | Bonzel | |
| 4,771,130 A | 9/1988 | Cohen | |
| 4,799,479 A | 1/1989 | Spears | |
| 4,807,620 A | 2/1989 | Strul et al. | |
| 4,824,436 A | 4/1989 | Wolinsky | |
| 4,835,258 A | 5/1989 | Hollenberg et al. | |
| 4,846,171 A | 7/1989 | Kauphusman et al. | |
| 4,878,492 A | 11/1989 | Sinofsky et al. | |
| 4,895,560 A | 1/1990 | Papantonakos | |
| 4,940,055 A | 7/1990 | Brown | |
| 4,957,481 A | 9/1990 | Gatenby | |
| 4,976,690 A | 12/1990 | Solar et al. | |
| 4,994,033 A | 2/1991 | Shockey et al. | |
| 4,997,431 A | 3/1991 | Isner et al. | |
| 5,002,531 A | 3/1991 | Bonzel | |
| 5,009,659 A | 4/1991 | Hamlin et al. | |
| 5,026,367 A | 6/1991 | Leckrone et al. | |
| 5,032,666 A | 7/1991 | Hu et al. | |
| 5,047,025 A | 9/1991 | Taylor et al. | |
| 5,053,033 A | 10/1991 | Clarke | |
| 5,057,106 A | 10/1991 | Kasevich et al. | |
| 5,061,273 A | 10/1991 | Yock | |
| 5,086,068 A | 2/1992 | Raleigh et al. | |
| 5,087,256 A | 2/1992 | Taylor et al. | |
| 5,092,841 A | 3/1992 | Spears | |
| 5,100,429 A | 3/1992 | Sinofsky et al. | |
| 5,102,402 A | 4/1992 | Dror et al. | |
| 5,106,386 A | 4/1992 | Isner et al. | |
| 5,109,850 A | 5/1992 | Blanco et al. | |
| 5,109,859 A | 5/1992 | Jenkins | |
| 5,120,322 A | 6/1992 | Davis et al. | |
| 5,126,140 A | 6/1992 | Ito et al. | |
| 5,156,594 A | 10/1992 | Keith | |
| 5,163,898 A | 11/1992 | Morcos et al. | |
| 5,171,217 A | 12/1992 | March et al. | |
| 5,171,264 A | 12/1992 | Merrill | |
| 5,197,946 A | 3/1993 | Tachibana | |
| 5,199,951 A | 4/1993 | Spears | |
| 5,207,670 A | 5/1993 | Sinofsky | |
| 5,217,482 A | 6/1993 | Keith | |
| 5,232,446 A | 8/1993 | Arney | |
| 5,236,410 A | 8/1993 | Granov et al. | |
| 5,263,992 A | 11/1993 | Guire | |
| 5,282,785 A | 2/1994 | Shapland et al. | |
| 5,286,254 A | 2/1994 | Shapland et al. | |
| 5,304,121 A | 4/1994 | Sahatjian | |
| 5,304,171 A | 4/1994 | Gregory et al. | |
| 5,324,750 A | 6/1994 | Lincoln et al. | |
| 5,445,608 A | 8/1995 | Chen et al. | |
| 5,470,307 A | 11/1995 | Lindall | |
| 5,482,719 A | 1/1996 | Guillet et al. | |
| 5,509,896 A | 4/1996 | Carter | |
| 5,555,889 A | 9/1996 | Karagueuzian et al. | |
| 5,571,151 A | 11/1996 | Gregory | |
| 5,588,962 A | 12/1996 | Nicholas et al. | |
| 5,609,575 A | 3/1997 | Larson et al. | |
| 5,612,050 A | 3/1997 | Rowe et al. | |
| 5,665,065 A | 9/1997 | Colman et al. | |
| 5,665,077 A | 9/1997 | Rosen et al. | |
| 5,695,460 A | 12/1997 | Siegel et al. | |
| 5,700,243 A | 12/1997 | Narciso, Jr. | |
| 5,709,676 A | 1/1998 | Alt | |
| 5,749,915 A | 5/1998 | Slepian | |
| 5,773,308 A | 6/1998 | Conrad et al. | |
| 5,788,678 A | 8/1998 | Van Antwerp | |
| 5,795,581 A | 8/1998 | Segalman et al. | |
| 5,797,887 A | 8/1998 | Rosen et al. | |
| 5,813,397 A | 9/1998 | Goodman et al. | |
| 5,817,144 A | 10/1998 | Gregory | |
| 5,830,539 A | 11/1998 | Yan et al. | |
| 5,836,940 A | 11/1998 | Gregory | |
| 5,840,059 A | 11/1998 | March et al. | |
| 5,843,073 A | 12/1998 | Sinofsky | |
| 5,843,789 A | 12/1998 | Nomura et al. | |
| 5,845,640 A | 12/1998 | Lawandy | |
| 5,848,177 A | 12/1998 | Bauer et al. | |
| 5,868,720 A | 2/1999 | Van Antwerp | |
| 5,925,012 A | 7/1999 | Murphy-Chutorian et al. | |
| 5,938,595 A | 8/1999 | Glass et al. | |
| 5,941,845 A | 8/1999 | Tu et al. | |
| 5,947,977 A | 9/1999 | Slepian et al. | |
| 5,954,706 A | 9/1999 | Sahatjian | |
| 5,991,650 A | 11/1999 | Swanson et al. | |
| 6,016,444 A | 1/2000 | John | |
| 6,053,887 A | 4/2000 | Levitas et al. | |
| 6,086,558 A | 7/2000 | Bower et al. | |
| 6,122,536 A | 9/2000 | Sun et al. | |
| 6,192,273 B1 | 2/2001 | Igel et al. | |
| 6,206,914 B1 | 3/2001 | Soykan et al. | |
| 6,228,393 B1 | 5/2001 | DiCosmo et al. | |
| 6,231,560 B1 | 5/2001 | Bui et al. | |
| 6,261,280 B1 | 7/2001 | Houben et al. | |
| 6,272,377 B1 | 8/2001 | Sweeney et al. | |
| 6,594,524 B2 | 7/2003 | Esteller et al. | |
| 6,599,281 B1 | 7/2003 | Struys et al. | |
| 6,631,291 B2 | 10/2003 | Vierto-Oja et al. | |
| 2002/0035338 A1 | 3/2002 | Dear et al. | |
| 2002/0156392 A1 | 10/2002 | Arai et al. | |
| 2002/0193670 A1 | 12/2002 | Garfield et al. | |
| 2003/0055355 A1 | 3/2003 | Viertio-Oja | |

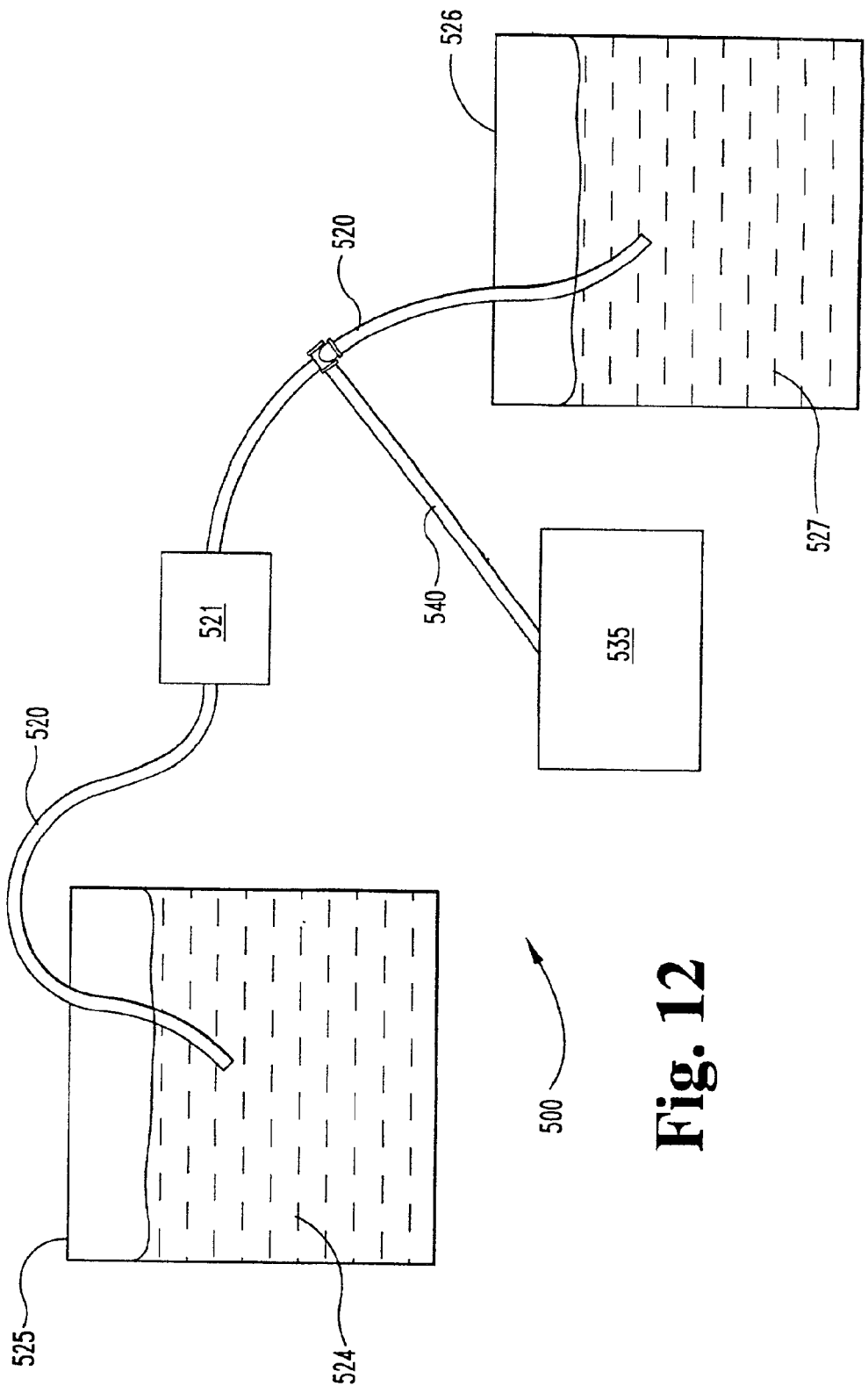

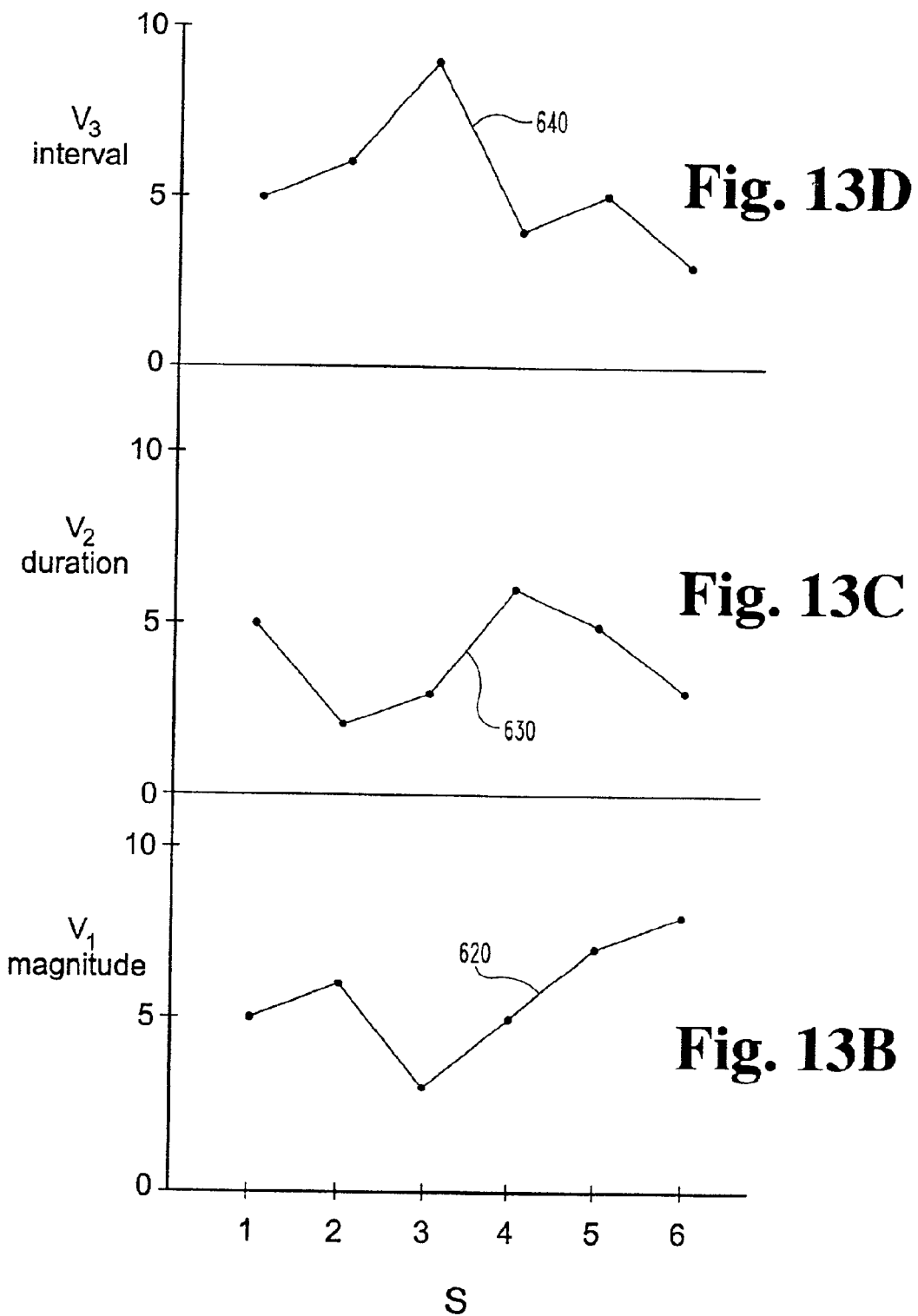

APPARATUS FOR THE CONTROLLABLE MODIFICATION OF COMPOUND CONCENTRATION IN A TUBE

CROSS REFERENCE TO RELATED APPLICATIONS

This application is a divisional of U.S. patent application Ser. No. 09/692,857, filed Oct. 20, 2000, now U.S. pat. No. 6,738,661. This application also claims priority to U.S. Provisional Patent Application Ser. No. 60/161,130, filed Oct. 22, 1999 and to U.S. Provisional Patent Application No. 60/170,051, filed Dec. 10, 1999. All of these applications are incorporated herein by reference.

FIELD OF THE INVENTION

This invention relates generally to the field of a tube with an internal layer comprising a polymer matrix and a captured compound, and more particularly to an apparatus for releasing a compound into an intravenous environment such as during intravenous drug administration.

BACKGROUND OF THE INVENTION

Invasive drug administration can be a difficult procedure to alter, once it is initiated. The dynamic nature of drug administration can be difficult to anticipate. Feedback mechanisms can be used to monitor drug administration and exert control mechanisms on the system.

As drugs are becoming more sophisticated and endogenous compounds continue to be discovered and synthesized, mechanisms to deliver drugs in a more exact and versatile fashion will allow for fuller drug utility to be realized.

Drugs have been released at the tip of solid catheters by applying laser energy as an aid in tumor or local drug therapy. Compounds have been encapsulated with the anticipation of releasing them in a controlled way for many years in the form of timed release capsules, matrix embedded tablets, or controlled release granules. A catheter product exists whereby an interior coating of antibiotic provides prophylactic protection against infection by providing zero order release of drug from the interior surface.

Standard drug infusion consists of employing infusate of constant concentration with respect to an active compound. The volumetric flow rate determines the rate at which a drug or compound is delivered to the systemic circulation or organ system. Altering the rate of drug delivery necessitates altering the volumetric flow rate of the infusate apparatus. Various catheter designs and drug delivery systems are described in U.S. Pat. Nos. 5,304,121; 5,482,719; 6,086,558; 5,991,650; 5,795,581; 5,470,307; 5,830,539; 5,588,962; 5,947,977; 5,938,595; 5,788,678; 5,868,620; 5,843,789; 5,797,887; 5,773,308; 5,749,915; 5,767,288; and 5,665,077.

The present invention overcomes the shortcomings of previous designs and systems in a novel and unobvious way.

SUMMARY OF THE INVENTION

One aspect of the present invention relates to a method for providing a compound into a first flowing material. The method includes providing a section of tubing having an interior with a layer of a second matrix material bonded to the interior, releasably capturing a first compound in the second matrix material, and flowing the first material through the interior and over the second matrix material. Energy is applied to the second matrix material, and the first compound is released from the second matrix material into the first flowing material.

In another aspect, the present invention includes a flexible outer sheath with an interior surface and an exterior surface. A polymer matrix is attached to the interior surface of the sheath, the polymer matrix defining a lumen therethrough for flow of the liquid. A therapeutic agent is releasably captured by molecules of the polymer matrix.

Another aspect of the present invention includes a method for manufacturing a catheter. The method includes providing a sheath with an interior surface, and applying a layer of matrix material onto the interior surface. The matrix material is in a swelled condition. A rod is inserted into the interior of the flexible sheath. The flexible sheath is formed into a predetermined shape, and volume of the polymer matrix is shrunk. The rod is removed.

Another aspect of the present invention concerns a method for manufacturing an internally coated tube. The method includes providing a rod and a sheath with an interior surface and an exterior surface. The method further comprises applying a layer of a polymer matrix onto the surface of the rod, and placing the rod within the interior of the sheath. The method includes forming the sheath into a predetermined shape around the rod and removing the rod from the formed sheath.

Another aspect of the present invention concerns a method for providing a therapeutic agent to a biological unit. The method includes providing a compound releasably captured within a matrix material, the compound being releasable upon receiving an energy input. The method includes placing the matrix material and captured compound in fluid communication with a fluid which flows in a biological space of the biological unit. Energy is provided to the matrix material sufficient to release a portion of the compound, and the compound is released into the biological unit in an irregular pattern.

These and other aspects of the present invention will be apparent from the description of the preferred embodiment, the claims, and the drawings to follow.

DESCRIPTION OF THE DRAWINGS

FIG. 12 is a schematic representation according to another embodiment of the present invention.

FIG. 13B is a graphical representation of the quantity of magnitude sampled at six regular intervals.

FIG. 13C is a graphical representation of the quantity of duration sampled at six regular intervals.

FIG. 13D is a graphical representation of the quantity of interval sampled at six regular intervals.

DESCRIPTION OF THE PREFERRED EMBODIMENT

Figure 1:
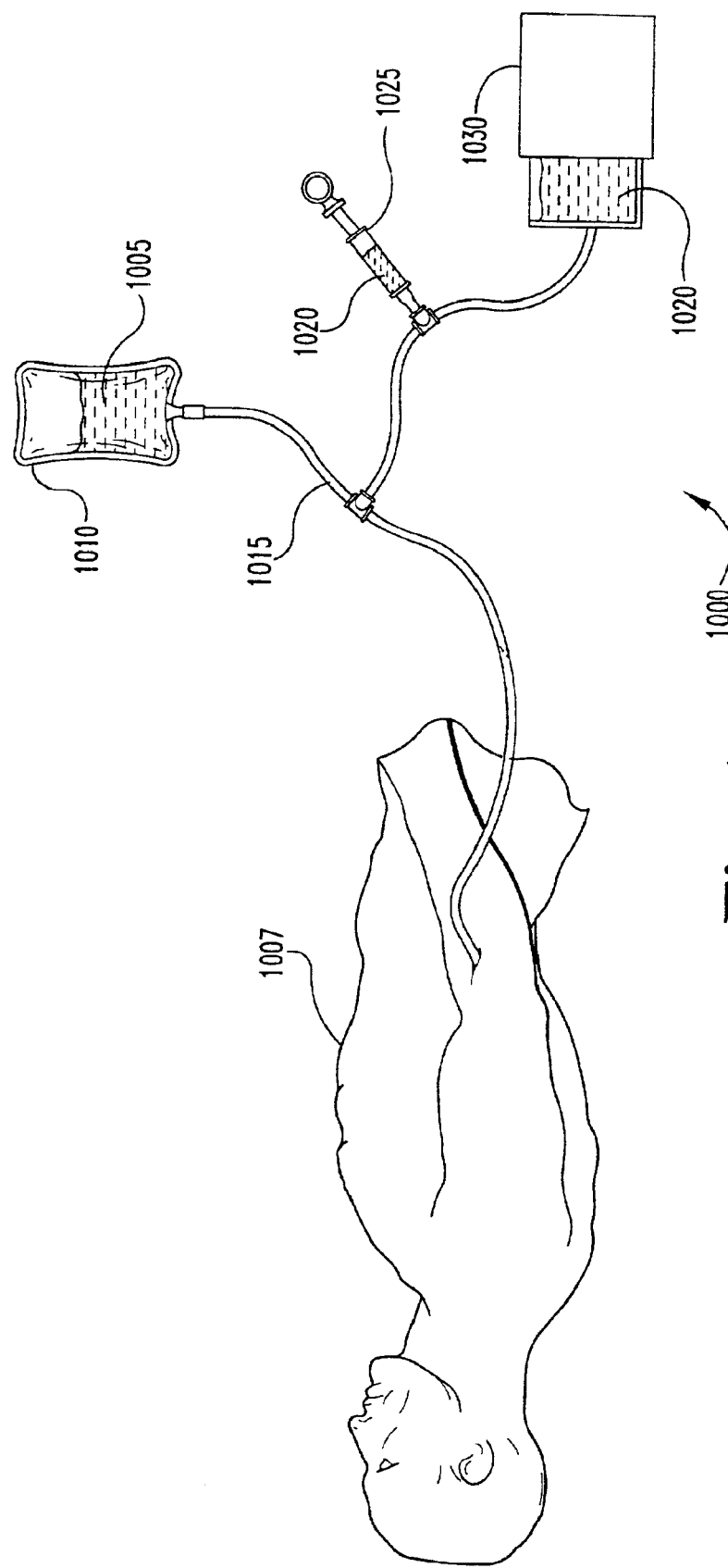
FIG. 1 is a schematic representation of a prior art system for delivering a drug by a catheter into a patient.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

All documents, including patents, books and other publications, named herein are incorporated herein to their complete extent by reference.

Turning first to FIG. 1 there is shown a typical infusion apparatus 1000 commonly in use in most modern hospital settings. This apparatus administers infusate 1005 systemically to a patient 1007. Infusate fluid 1005 is contained in a plastic bag 1010, and the fluid is allowed to pass at some predetermined volumetric flow rate through plastic tubing and catheter setup 1015 and into an appropriate biological space, usually vascular. This space could be other body spaces or cavities capable of accepting positive volumetric flow, such as the peritoneum or cerebral spinal fluid space. This defines an "open" space or cavity as opposed to a closed or site specific location. Examples of other open spaces include the systemic circulation, the lymphatic space, synovial fluid spaces and urinary fluid spaces.

Administration of a compound or drug 1020 is accomplished in several ways. For example, the drug 1020 may be manually injected by an attendant through a hand syringe 1025 that is in fluid communication with catheter 1015. As another example, a pump 1030 containing a quantity of drug 1020 pumps a controlled quantity of the drug into an apparatus that is in fluid communication with catheter 1015. Maximum maintenance of the sterile environment of the system is realized.

The amount of drug administered is directly related to the infusate flow rate and the concentration of compound (drug) in solution with the infusate. Changing the rate of infusion of drug necessitates changing the volumetric flow rate of infusate through the catheter in direct proportion to the desired change in drug administration. Once the infusion setup is operating, generally under sterile conditions, changing the compound or drug for an alternate compound or drug requires a new infusion setup to be put into operation, with a new reservoir of infusate with drug in solution.

The present invention relates to a system including a catheter assembly and a source of energy for releasing a compound into a biological space, such as the vascular system, peritoneum, cerebral spinal fluid space, or other biological spaces which can accept a volumetric flow rate of infusate. According to one embodiment of the present invention, a therapeutic agent such as a drug is linked by photolabile bonds to a polymer matrix surrounding a lumen of a catheter. Infusate fluid such as normal saline, 5% dextrose and water, lactated Ringer's solution, crystalloid solution, plasma or blood flows through the lumen of the catheter from a source of the infusate into the biological space. When it is desired to release the compound into the biological space, the polymer matrix surrounding the lumen and including the photolabily-linked compound is exposed to energy such as light radiation. The radiation breaks the photolabile bonds, and the compound is released from the material such that it can diffuse into the infusate.

Changing the concentration of infusate without appreciably changing the volumetric or mass flow rate is contemplated by this invention. Some infusate apparatus only allow volume dependent alteration of dosing rate, which may be prohibitive to the recipient. It may be difficult to readily add or change pharmacotherapy due to insufficient vein integrity. The immediacy of emergency settings may dictate drug to be administered as readily as possible, or discontinued in as immediate a fashion as possible.

The present invention can provide an effective and efficient mechanism to exert an infusate concentration change for a compound delivery system with little or no volumetric changes. The clinical setting is an example where compounds can be introduced by varying the concentration profile of a drug to alter the dose or mass of drug administered. This is a departure from the traditional manner of increasing the volume flow rate of intravenously administered drugs. The ease and rapidity of introducing new compounds to a given drug therapy provided by the present invention may be unmatched for some settings. In-line prodrug-drug interactions are possible. Developing drugs with previously prohibitive delivery characteristics, such as extremely short half-lives, may be delivered with this device.

In a preferred embodiment, the material forming the lumen of the catheter is a polymer such as a hydrogel, and the one or more compounds to be released are photolabily-linked to the molecules of the hydrogel. The compound(s) to be released are preferably therapeutic agents which are released systemically into the biological space. The photolabile linkages between the compound and the hydrogel are preferably broken by resonating the photolabile bond with the proper wavelength of radiation. In a preferred embodiment, the source of radiation is a laser tuned to a band of wavelengths that will resonate with the photolabile links. However, the present invention also incorporates those embodiments in which the source of radiation includes lasers operating over wide ranges of wavelengths and also incoherent light.

Another embodiment of the present invention includes a catheter assembly including a material defining a lumen, a photolabily-linked compound within that material, a source of infusate flowing through the lumen, and a source of energy. The embodiment further includes a sensor for sensing a condition of a biological subject and a controller for receiving the signal. As one example, a source of radiation, such as a laser, is activated to irradiate the material, break the photolabile bonds, and release the compound into the biological subject upon the sensing of a particular condition. As another example, the sensor generates a signal corresponding to the activity of the heart. The controller receives this signal and upon determination that the heart is malfunctioning controls the laser to release a drug such as a cardiac agent into the infusate, which then flows into the biological space of the subject so as to address the heart malfunction.

A wide range of therapeutic agents can be incorporated in complexes for controlled release into the systemic circulation or other body cavity of a biological subject. It is preferable that the chemical structure of the therapeutic compound contain a nucleophile group such as carboxylic acid, amino or hydroxyl, which attaches to the light sensitive linkage of the polymer matrix material defining the catheter lumen. Examples of such therapeutic compounds include acetylsalicylic acid (aspirin), indomethacin, nicotinic acid, naproxen, ibuprofen, cimetidine, ranitidine, cycloserine, flucytosine, amantadine, benzocaine, penicillin V, acetaminophen, and cortisone. Classes of drugs amenable to this type of delivery include, but are not limited to antibiotics, anesthetics, analgesics, cardiac agents, psychotropics, and hormones.

Although what has been described is a catheter flowing infusate, the present invention also contemplates the application of a compound releaseably captured in a matrix material applied to the inside of tubing, where a flowing material flows through the tubing and over the matrix material. The flowing material may be a fluid, such as a liquid or a gas and can also be a flow of solid particulate matter such as an aerosol or solid microparticles. Further, the matrix material for releaseably capturing a compound is preferably a polymer material, but can also be other types of matrix material. The compound releaseably captured in the matrix can be a therapeutic agent, but can also be any compound capable of being releaseably captured in the matrix.

As used herein, the term "catheter" includes those meanings and definitions and understandings used by one of ordinary skill in the art, but also includes tubing for withdrawal of bodily fluid from a biological unit. Further, the term "therapeutic compound" as used herein refers to drugs and compounds administered to biological units, and also refers to drugs and compounds used to condition fluids withdrawn from a biological unit. The use of a prime (') designation with a number indicates that the element shown or described is the same as the non-prime element, except as shown or described differently.

Figure 2:
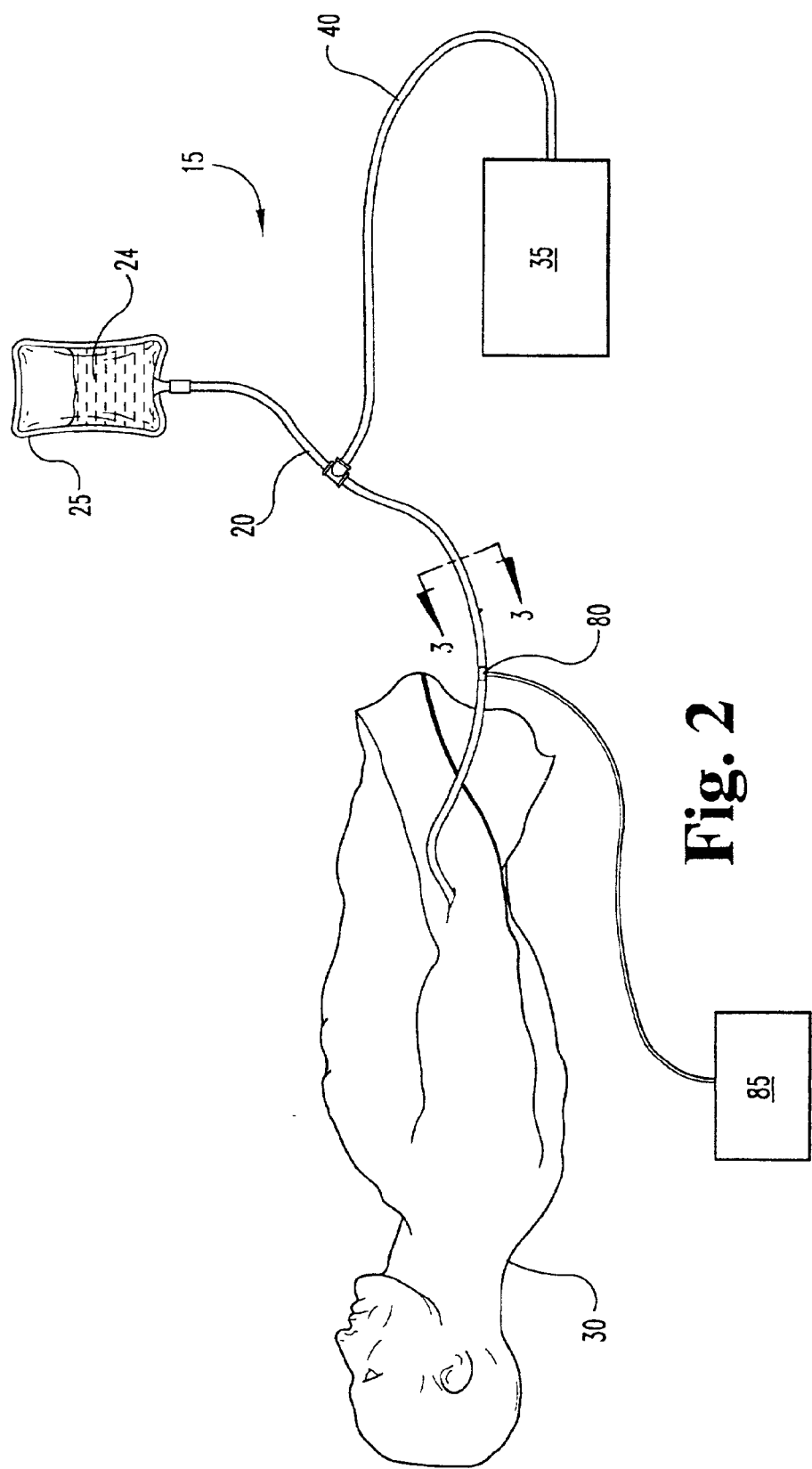
FIG. 2 is a schematic representation of one embodiment of the present invention for providing a therapeutic agent into a biological unit by a catheter.
Figure 3:
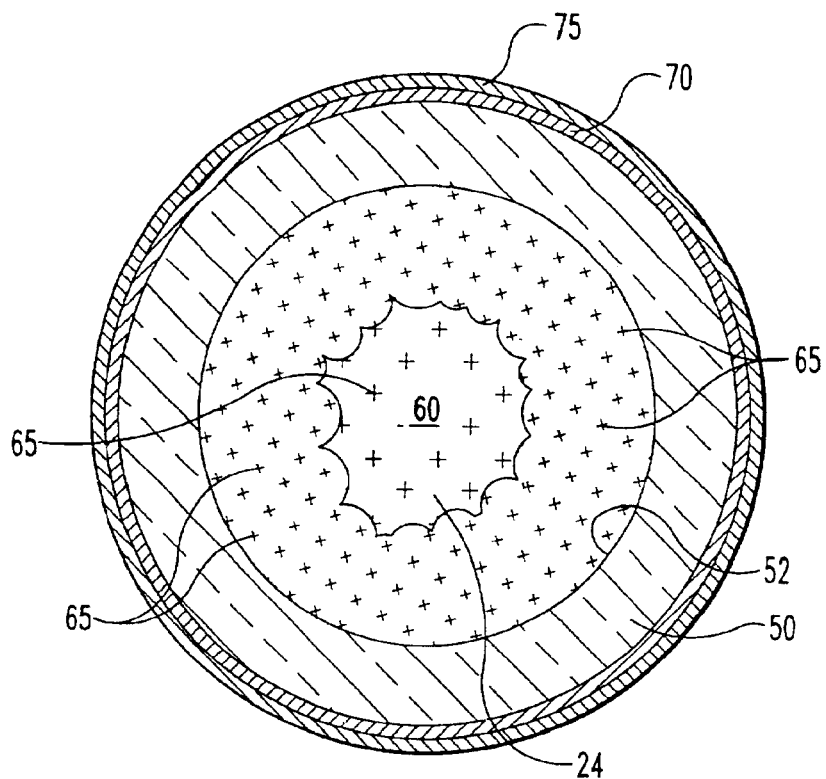
FIG. 3 is a cross-sectional view of the catheter of FIG. 2 as taken along section 3—3 of FIG. 2.

Turning to FIGS. 2 and 3, a catheter is constructed to release a therapeutic compound 65 into the infusate 24 flowing in the catheter 20 during the infusion process. In one embodiment, the catheter size is similar to conventional vascular catheters used in hospitals of today. As used herein, the term catheter includes any generally tubular medical device for insertion into canals, vessels, passageways, or body cavities for the reception or withdrawal of fluids through the catheter lumen. A catheter, according to the present invention provides additional therapeutic properties to the infusate 24 as it travels through the catheter lumen space 60. Conventional catheter designs that may be adapted for delivery of a therapeutic agent according to the inventions described herein include, but are not limited to, percutaneous transluminal angiography (PTA) catheters, percutaneous transluminal coronary angioplasty (PTCA) catheters, vascular and peripheral vascular catheters, thrombectomy catheters, renal catheters, esophageal catheters, perfusion catheters, upper and lower gastrointestinal catheters, bile duct and pancreatic duct catheters, urogenital catheters, and similar catheters both with and without dilation capabilities. Devices used for long-term vascular access may be adapted for use with the present invention. These catheters include, but are not limited to totally implantable intravascular devices (TIDs), tunneled central venous catheters including Hickman, Broviac, Groshong, and Quinton, which are commonly used to provide vascular access to patients requiring prolonged IV therapy (e.g., chemotherapy, home infusion therapy, hemodialysis).

FIG. 2 schematically depicts a system 15 according to one embodiment of the present invention. System 15 includes a catheter assembly 20 which provides a flow of infusate 24 from an infusion apparatus 25, such as a gravity drip bag, into the open biological space of a biological unit 30, such as into the vasculature of a patient. An energy source 35 is coupled by an appropriate conduit 40 into catheter 20. Energy source 35 provides energy through conduit 40 to a polymer material within catheter 20. In one embodiment of the present invention, energy source 35 includes a laser, laser controller, and controller interface. The laser provides coherent light energy to a conduit 40 such as a fiberoptic cable to transmit the laser energy into the catheter 20.

FIG. 3 shows a cross-section of catheter assembly 20. Catheter 20 includes a sheath 50 forming the basic structure of assembly 20 and capable of transmitting energy from source 35. Located within the interior of sheath 50 is a polymer matrix 55 which forms a lumen 60 therein. Infusate 24 from infusion apparatus 25 flows through lumen 60 into the biological space. Polymer matrix includes within it one or more therapeutic agents 65 that are held within the polymer matrix 55 until released by energy from source 35. According to one embodiment of the present invention, the linkage of the therapeutic agent 65 to the polymer matrix 55 is accomplished by a covalent photolabile bond. The transmission of laser energy through sheath 50 provides energy that breaks the photolabile bond to release the therapeutic agent. The therapeutic agent then defuses according to Fick's Law through the polymer matrix and into the infusate flowing within lumen 60. In this manner the therapeutic agent can be stored within polymer matrix 55 until it is desired to release therapeutic agent 65 into the biological unit. For those embodiments of the present invention utilizing a source of energy such as a laser, sheath 50 includes one or both of a reflective coating 70 and/or an opaque coating 75.

Although what has been shown and described is a catheter 20 extending from a source 25 of infusate into the vasculature system of a biological unit, the present invention also contemplates the use of a catheter 20 which is linked as an input to a separate catheter, such as catheter 1015. The separate catheter may be made of any size and shape which facilitates entry of the separate catheter into the biological unit. The separate catheter and catheter 20 are joined in a union outside of the body of the biological unit. This alternate embodiment permits catheter to have an outer diameter and/or use materials not compatible with entry into a biological unit.

A catheter assembly 20 according to one embodiment of the present invention has both drug storage and drug releasing properties, and the ability to transmit appropriate energy from a source of energy 35 into polymer matrix 55. A photo-activateable therapeutic agent delivery material is used, in which a therapeutic agent 65 is combined by covalent bonding, incorporation in a matrix, or encapsulation, with a photosensitive macromolecule. In this combination, the drug is inert. The macromolecule is large enough to prevent migration of the combination within the catheter body, so that the combination can be in place during infusion or withdrawal of bodily fluids through the luminal space. A drug or other compound is released from the combination, in an active form, upon appropriate stimulation by the source of energy 35.

The drug may be combined with the polymer matrix using any of several mechanisms including photolabile chemical bonding, physical dispersion, or encapsulated or embedded in layers of photodegradable polymers. In preparing the covalent chemical complex of this aspect of the present invention, it is preferred to link the photolabile compound to the polymer 55 first, and to link the drug 65 to the photolabile groups thereon subsequently. Coupling of the polymer 55 to the photolabile linking compounds suitably takes place in solution, as does the subsequent coupling of the photolabile linking compounds to the therapeutic agent.

A wide choice of polymers 55 are available for this purpose. It is desirable that the polymer be biochemically acceptable and inert. It is further desirable that the polymer should possess chemical groups capable of reaction with a functional group of the photolabile compound such as the carboxylic acid group of BNBA or CPA, e.g. hydroxyl groups. It should also be capable of releasing the active drug freely, once the covalent chemical bonding has been broken. For example, the drug 65 should be able to diffuse out of the residual polymer matrix in the presence of infusate fluid. Examples of suitable polymers 55 include, but are not limited to polyvinyl alcohol (PVA), polyethylene oxide (polyethylene glycol PEG), acrylamide copolymers, vinylpyrolidone copolymers, hydroxyl functionalized polylactides, poly hydroxyethyl methacrylate (HEMA), copolymers of two or more such monomers, e.g. copolymers of vinylpyrrolidone and HEMA, and copolymers of ethylene oxide and propylene oxide. The hydrogel polymer may also be selected from the group consisting of polycarboxylic acids, cellulosic polymers, gelatin, polyvinylpyrrolidone, maleicanhydride polymers, polyamides, polyvinyl alcohols, and polyethylene oxides or polyacrylic acid.

The catheter sheathing material is a homogeneous fiber optic material that is transparent to and is able to conduct the controlling energy, preferably laser light, throughout the extent of the molded sheath. The fiber optic material is of a type known to the art of laser catheters and is configured to transmit laser energy. A person of ordinary skill in the art can readily adapt known fiber optic materials for incorporation into the apparatus of the present invention. A hydrogel matrix forms a large portion of the body of the catheter tubing and is tenaciously affixed to the inner surface of the energy-conducting sheath. This matrix provides the storage space for photolabily linked compound to remain in a soluabilized and bound state prior to compound release via controlled delivery of energy through the sheathing material.

The hydrogel polymer matrix 55 deposition and affixation to the inner surface 52 of the catheter sheath 50 can be accomplished by the following example according to U.S. Pat. No. 5,304,121, incorporated herein by reference. The inner surface 52 of the catheter sheath 50 is coated with a solution of 4,4' diphenylmethane diisocyanate (MDI) in methylethylketone for 30 minutes. After drying in an air oven at 85° C for 30 minutes, the sheath is dipped in a 1.7% solution of poly(acrylic acid) homopolymer having a molecular weight of about 3,000,000 in dimethylformamide (DMF) and tertiarybutyl alcohol. After drying at about 85° C. for 30 minutes, a smooth coating is obtained. The sheath is oven dried for 8 hours at 50° C. One function of the drying steps is to remove solvent from the coating. The polyisocyanate solution is at a concentration of about 0.5 to 10% by weight. The polyacrylic acid is at a concentration of about 0.1 to 10% by weight. The poly(carboxylic acid) to polyisocyanate molar ratio is generally about 1:1. The formation of the hydrogel is well known in the art, such as the hydrogel further described in U.S. Pat. No. 5,091,205, incorporated herein by reference.

The rate of drug release is controlled by exposure of the catheter body to a source 35 of transmissible energy, such as the energy of a laser. Persons of ordinary skill in the art know readily available electronic devices which can be used for laser energy generation and computer control. Through suitable optical coupling 40, the laser energy enters the catheter sheath or casing 50, and in a preferred embodiment, is reflected off of the reflective outer coating 70 and is transmitted into and through the catheter body when it is desired for drug to be released from catheter matrix material storage. Photolabile bonds are broken and the freed therapeutic agent 65' is released and traverses across the infusate soluble polymer matrix material 55, and into the catheter lumen 60 as free therapeutic agent in infusate solution 24. An outer opaque coating 75 with reflective properties prevents extraneous light from entering the catheter-body and also directs the controlled laser light into the catheter body to provide energy exposure.

Energy for release of the drug in its active form from the drug-polymer combination can be by one of a variety of means depending upon the photosensitivities of the chosen photolabile bond, the polymer 50, and the drug 65. For example, the source 35 of energy can be radiation such as infrared, visible, or ultraviolet radiation, supplied from incandescent sources, natural sources, lasers including solid state lasers, or even sunlight. In one embodiment, the present invention contemplates the use of a source 35 of coherent light of wavelengths from about 300 nm to about 1200 nm. This includes UV, visible and infrared light. The choice of wavelength is based on the photolabile characteristics of the bonds holding 65 within 55 and is selected to match the wavelength necessary to break the photolabile bond between 65 and 55. Since body tissues tend to absorb radiation in the ultraviolet region of the electromagnetic spectrum, it is preferred to choose a photolabile bond sensitive to red and infrared wavelengths. The amount of drug released is proportional to the dosage of the radiation. Various agents for producing the photolabile bonds are described in related art such as U.S. Pat. No. 5,767,288, incorporated herein by reference.

Administration of the radiation can be by use of fiber optic light pipes or sheathing included within the catheter assembly. Fiber optic light pipes 40 are known and used in various types of medical treatments, for example irradiation treatment of internal body organs such as bladder irradiation. In some embodiments of the present invention, a fiber optic light pipe also acts as the main source of energy into matrix 55, the light pipe providing light down the length of catheter 20 and transmitting the light radially or longitudinally through the catheter sheath. These light pipes can be used to couple energy of particular wavelengths to distinct sections of the sheathing material.

Preferably, the apparatus comprises an optically transmitting fiber optic outer sheath 50 having a proximal end and a distal end. The material can be either transparent or translucent. The preferred material is transparent and non-distendable. The fiber optic sheath 50 is of a type known in the art of laser catheters and is configured to transmit laser energy. The intensity and overall uniformity of the light transmitted can be dramatically increased by using a coating 70 that reflects and/or scatters light into the lumen 60. The sheath 50 preferably includes a reflective outer coat 70 that reflects and scatters light into and through the polymer matrix 55 and into the lumen 60, providing a diffuse reflection of the light striking the matrix 55 and agent 65. The function of the reflective material is to provide increased uniformity and efficiency in the light transmitted through polymer matrix 55. Examples of material for coating 70 include, but are not limited to, titanium dioxide, aluminum, gold, silver, and dielectric films. A person of ordinary skill in the art can readily adapt known reflective materials for incorporation into the outer portion of the apparatus of the present invention. The preferred reflective material will reflect and scatter light and prevent from about 20% to 100% of light striking the material from passing through the material. The most preferred will reflect and scatter over 70% of the light. The reflective material can be incorporated onto the outer portion of the sheath 50 in a variety of ways. For example, the reflective material can be applied to the outer surface of catheter sheath 50 after the catheter is formed, by using a dipping process. Alternatively, the reflective material can be directly incorporated into the material used to form the catheter sheath 50 during the manufacturing. The method used to incorporate the reflective material into the catheter is based primarily on the reflective material used, the material the catheter is made of, and the method used to manufacture the catheter. A person of ordinary skill in the art can readily employ known procedures for incorporating a reflective material within or onto the surface of the catheter sheath 50.

In addition to a reflective coating, the catheter may further have an additional opaque coating 75 over the reflective coating 70. An opaque coating 75 is used to further prevent light from exiting the catheter exterior surface or extraneous light from entering the body of the catheter. Some catheters, such as those disclosed by Overholt et al. *Lasers and Surgery in Medicine* 14:27–33 (1994), utilize an opaque absorbing coating, such as black Color Guard supplied by Permatex Industrial Corp. Avon, Conn., to prevent the light from being transmitted through portions of the catheter.

Some embodiments of the present invention further include one or more optical sensors 80. Optical sensors 80 are integral to the catheter and used to measure the intensity of illumination when the catheter is used therapeutically. Optical sensors 80, such as a fiber optic probe or a photodiode as part of a balloon catheter, have been described in U.S. Pat. No. 5,125,925, incorporated herein by reference. By monitoring, with a sensing fiber on the wall of the fiber optic sheath, the light to which the sensing fiber and, hence, the catheter matrix are exposed, can be determined. Individual light doses and accurate measurement of the cumulative light doses are measured by processor 85 and provide an accurate measurement of the cumulative light dose and relates to released compounds from various sections of the catheter matrix or associated sections of the catheter matrix. Light power output is also monitored and alarm may be given in the event of abnormal light conditions.

In accordance with the present invention, therapeutic agent 65 is stored within the polymer matrix 55. Once the infusate is flowing through lumen 60 at a constant rate and the matrix is in a hydrated condition, the therapeutic agent 65 is in a soluablilized state within the polymer matrix, with respect to the surrounding infusate fluid infiltrate. A barrier to complete drug solution in the infusate are laser liable bonds holding the therapeutic agent 65 within the polymer matrix 55. These bonds can be broken when exposed to the proper frequency and intensity of laser energy, thereby freeing the drug to enter the catheter lumen 60.

Figure 4:
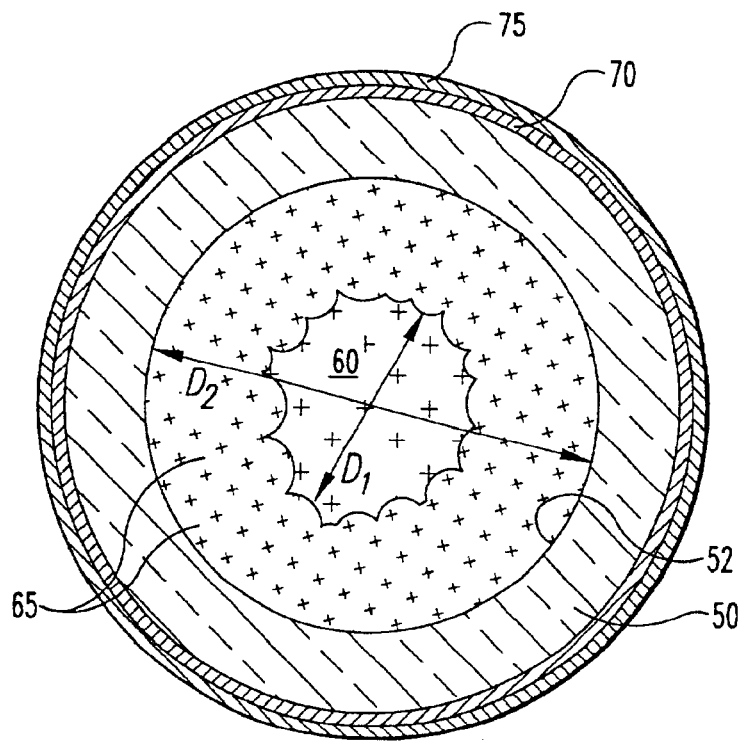
FIG. 4 is a cross-sectional view of FIG. 3 including the designation of diameters for calculation of the amount of therapeutic agent within the polymer matrix.

The amount of storage volume is adequate to incorporate a substantial amount of drug to be used for various procedures. As best seen in FIG. 4, in one embodiment of the present invention the inner wall 52 of sheath 50 has a diameter $D_2$ of about 3.6 mm, and the lumen formed by polymer matrix 55 has a diameter $D_1$ of about 2.6 mm. The total length $L_1$ of the portion of the catheter 20 incorporating the polymer matrix is 1.7 meters. The cross-sectional area Al is calculated as $\pi(D_2^2 D_1^2)/4$ and is 4.84 mm$^2$. The total volume $V_1$ of the polymer matrix is 8.23 cm$^3$. This is a representative volume calculation and provides an estimate of a catheter body matrix 55 volume that would be available for drug incorporation for the present invention. There is no general restriction of the tubing diameter of the portion of the present invention that resides outside the vasculature. It is anticipated that an 8–12 cm$^3$ volume of catheter matrix material 55 would be sufficient to incorporate substantial amounts of drug(s) into the polymer matrix for delivery into the infusate and further into the systemic circulation or receiver space. Much larger reservoirs for drug storage can be realized for portions of the present design to be extravascular in nature. By controlling the concentration of the therapeutic agent 65 within matrix 55, the total amount of therapeutic agent 65 available for infusion can be limited by control of the thickness and length of the polymer matrix. For example, the total amount of therapeutic agent stored in a particular catheter assembly 20 can be limited to an amount that is safe for delivery under any conditions. Jacketed conditioning of the tubing extravascularly, such as for temperature or radiation exposure, can also be provided for extravascular portions of the present invention to allow for better inline processing of fluids or for maintaining the integrity of the catheter body matrix or compounds stored therein.

Figure 6:
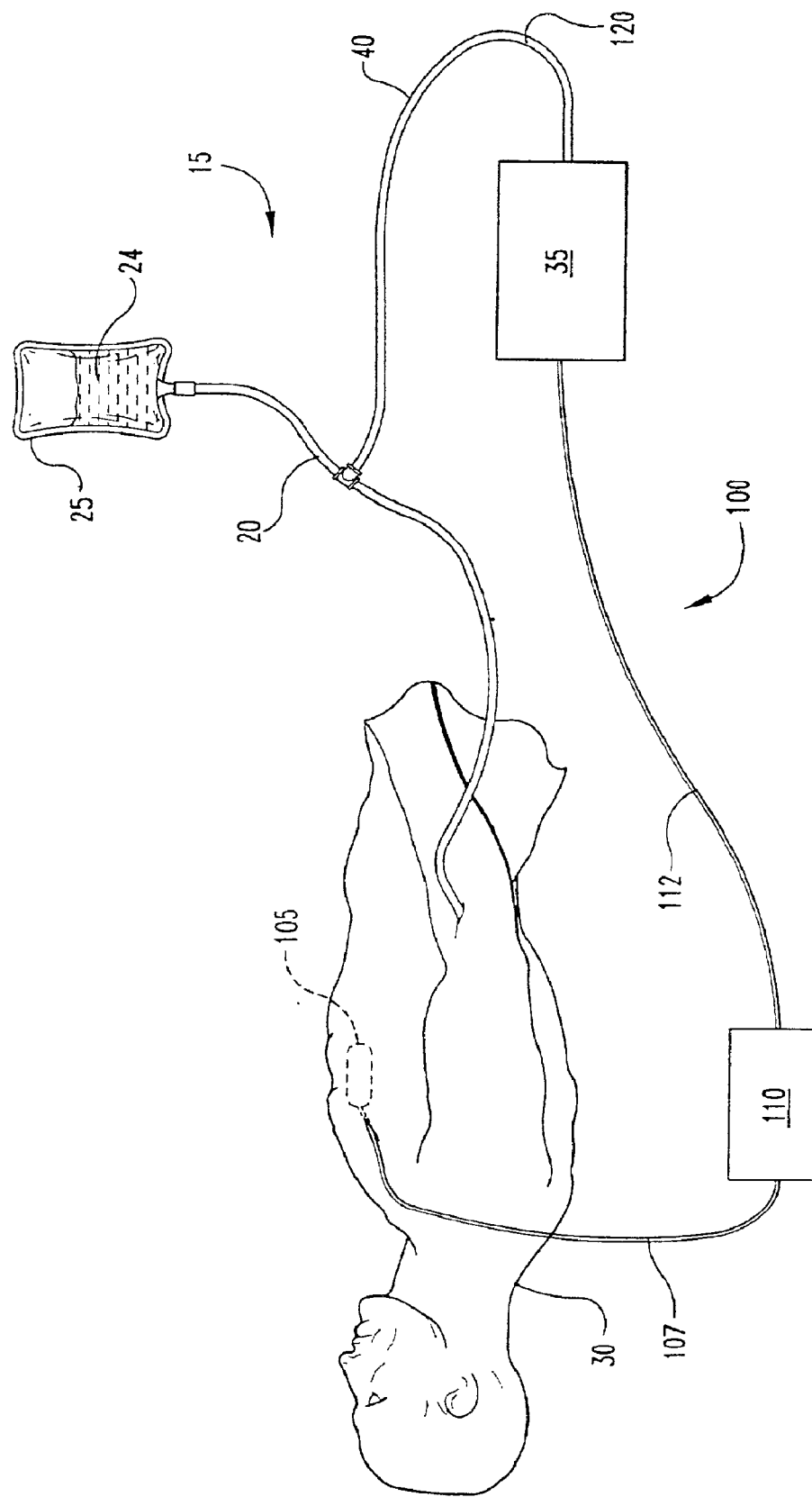
FIG. 6 is a schematic representation of a closed-loop system for providing a therapeutic agent to a biological unit.

FIG. 6 depicts a system 100 for the automatic administration of a therapeutic agent based on a sensed response from a biological unit A biological unit 30 such as an animal produces a response which can be sensed by a sensor 105. The response elicits an output signal 107 which is provided to a signal processor 110. Signal processor 110 preferably accepts analog signal 107, and includes suitable A/D processing and an internal digital processor which produces a control signal 112 to energy source 35, such as a laser. In response to control signal 112, energy source 35 produces an energy output 120 which is coupled into catheter 20. Energy response 120, which is preferably a controlled amount of laser light, is transmitted down the fiber optic sheath 40 of catheter assembly 20 and fractures the bonds between the therapeutic agent 65 and polymer matrix 55. The release of the therapeutic agent into the infusate and subsequently into the biological unit 30 changes the response of the biological unit that resulted in the signal 107 generated by sensor 105. Another example, sensor 105 measures the brain activity of a person during anesthesia and provides a signal to an electroencephalographic monitor 110. If the depth of anesthesia is determined through brain wave activity to be aberrant, then a signal is sent to a power supply to fire a laser and release a therapeutic anesthetic agent from the catheter into the blood stream of the patient.

As one example, sensor 105 measures the cardiac activity of a person and provides a signal to a cardiac monitor 110. If the cardiac monitor 110 determines that the patient is in cardiac distress, then a signal is sent to a power supply to fire a laser and release a therapeutic cardiac agent from the catheter into the blood stream of the patient.

Figure 10:
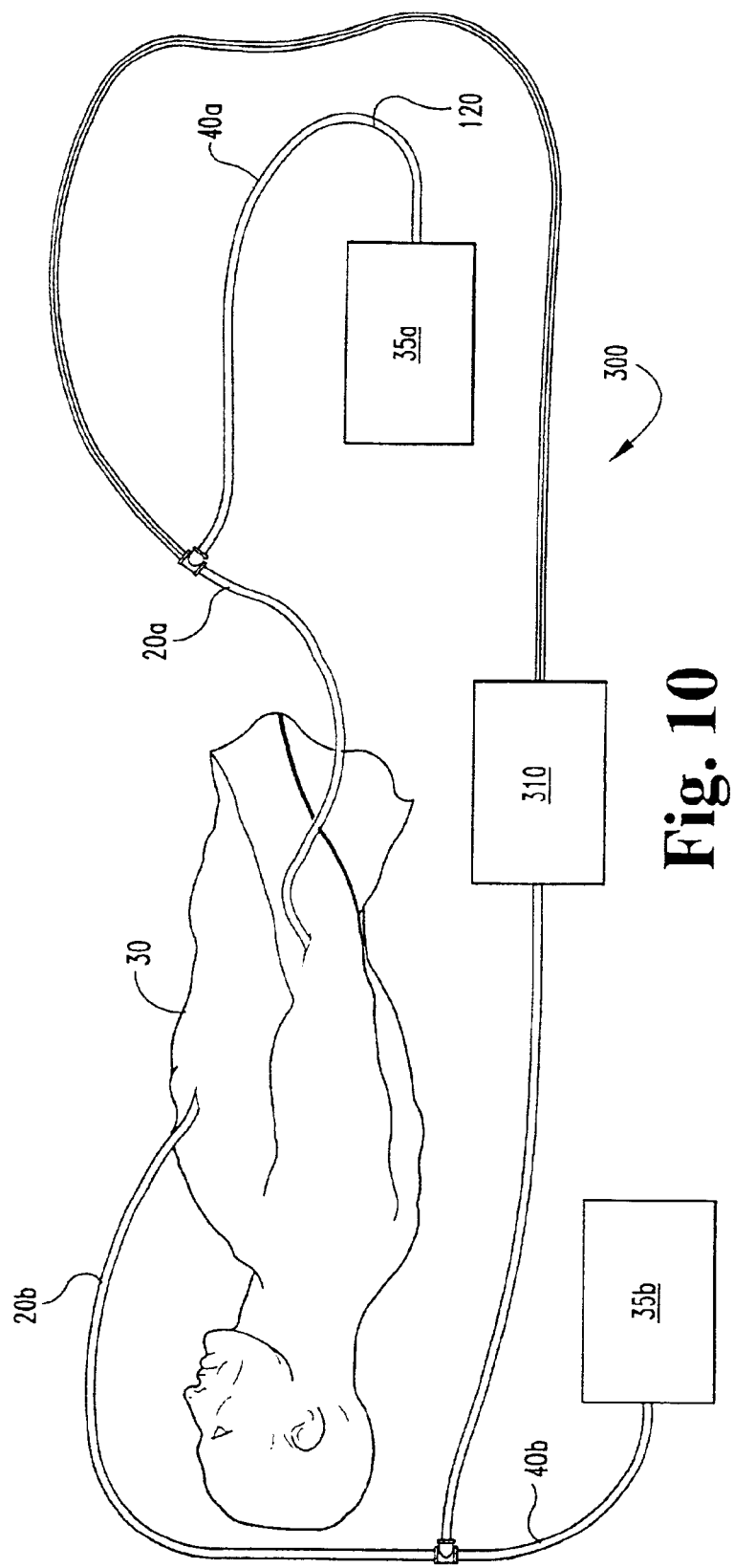
FIG. 10 is a schematic representation according to another embodiment of the present invention for withdrawal of fluid from a biological unit and return of the fluid to the unit.
Figure 11:
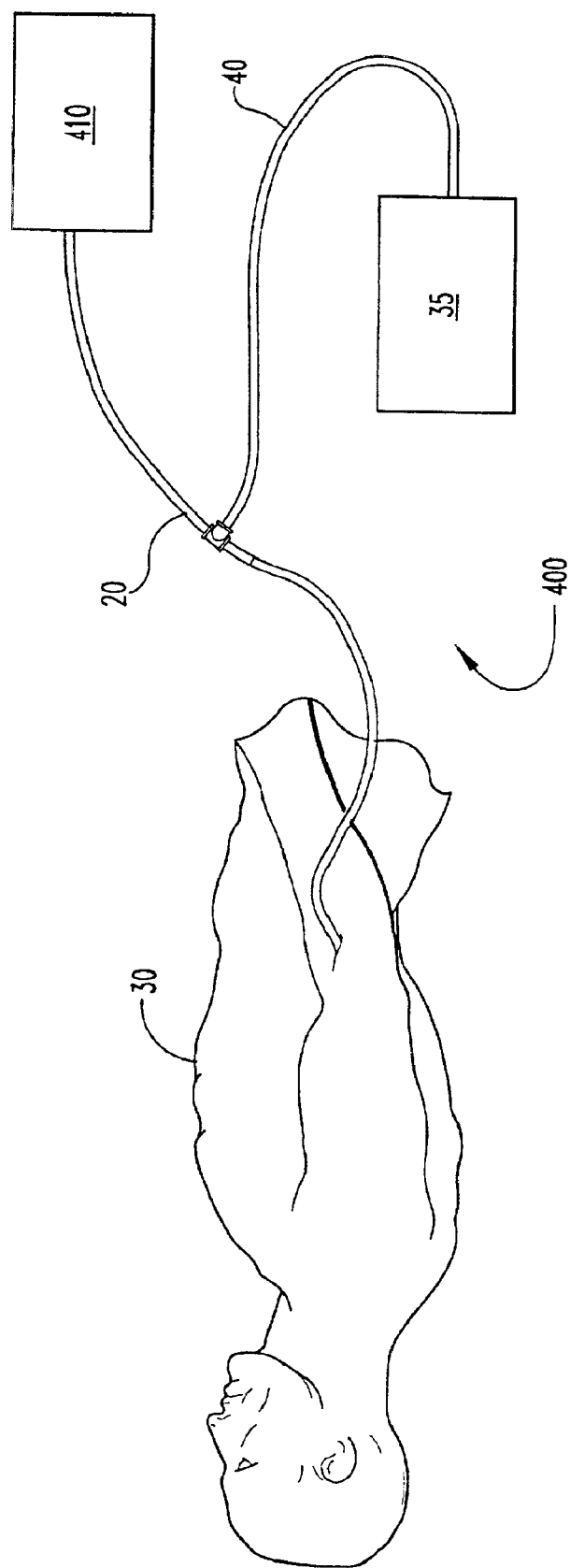
FIG. 11 is a schematic representation according to another embodiment of the present invention for withdrawal of fluid from a biological unit.

The present invention may be used during outflow of bodily fluids from a body cavity. FIGS. 10 and 11 schematically depict systems for the withdrawal of bodily fluids from a biological unit. The exit of fluid from the body during kidney or peritoneal dialysis would be examples of this use. A device 310 for withdrawal of fluids, such as dialysis machine, is in fluid communication with catheter 20a. A compound captured within the polymer matrix of catheter 20a is released by energy from energy source 35a as transmitted along conduit 40a. The bodily fluid is further conditioned within conditioning unit 310, which is in fluid communication with a catheter 20b for return of the fluid into the biological unit. Another therapeutic agent captured in the polymer matrix of catheter 20b is released into the bodily fluid by activation of energy source 35b which provides energy through conduit 40b into the sheath of catheter 20b.

The catheter or tubing 20 would release compound into contents of body fluid, such as, blood, cerebral spinal fluid, cardiac pericardial fluid, lymph, during outflow, adding pretreatment compounds, such as anticoagulant, antibiotic, anti-thrombotic or other conditioning or treatment agents proximal to entrance into the dialysis or other equipment. Upon exit from a treatment apparatus, such as dialysis or chemotherapy devices, and prior to return into the living system, further conditioning compounds could be released into the luminal tubing space to deactivate or activate functionalities in the treated body fluids. The advantage of maintaining sterile or otherwise separate conditions during such extra-corporal closed loop treatments is realized. It is anticipated that the tubing designed from the present invention could be incorporated into the interior of an apparatus for dialysis or other inline treatment regimen, such as during lymphatic or leukemic cancer treatment or other disease amenable to fluid treatment modalities. The permanent withdrawal of fluids for diagnostic sample collection can be pretreated during collection with another embodiment of the present invention. As seen in FIG. 11, system 400 withdraws bodily fluid from a biological unit and conditions that fluid for subsequent use during testing or analysis of the fluid. Fluid is withdrawn from a biological unit 30 through a catheter 20 which is in fluid communication with a fluid receiver 410, receiver 410 including a suction pump or other means for withdrawing fluid. As the fluid passes through catheter 20, energy source 35 provides energy through conduit 40 into the polymer matrix of catheter 20, such that a compound releasably captured in the polymer matrix is released into the bodily fluid flowing into receiver 410. For example, the bodily fluid can be blood, and the compound released from the polymer matrix can be an anticoagulant. Addition of anticoagulant, antibodies, or dyes prior to sample preparation can aid in the accuracy, reliability and speed of such clinical testing. This sample conditioning could extend to any sample fluid obtained through such tubing, including lymph, CSF, certain biopsy material and urine. It is also anticipated that various laboratory, experimental, industrial or non-biological processes or settings can incorporate the present invention and method thereof for the purposes of adding compounds to an inline process.

It has been shown (U.S. Pat. No. 5,482,719) that a shape retaining non-flowing aqueous hydrogel polymer and drug compound PEG 6000-BNBA-nicotinic acid released unchanged nicotionic acid upon irradiation with light. The anti-viral drug adamantamine was coupled to a polymer via a photolabile chemical linkage utilizing the amino group of the drug, and then released in unchanged form by photolysis 8 mg of the 10 mg of adamantamine combined with the hydrogel-photolinker present in the formed hydrogel-linker-drug yield of ADANABA-Et. This complex released unchanged adamantamine over a ten minute period with most of the drug being released within 5 minutes and with only a trace amount left complexed after ten minutes of irradiation.

The present invention also contemplates non-biological embodiments. FIG. 12 is a schematic representation of system 500 according to another embodiment of the present invention for releasing a compound into a fluid flowing from one container into another container. A fluid 524 held within a container 525 is removed from container 525 by a pump 521. The pump 521 provides the fluid to a section of tubing 520 which contains an internal layer of a matrix material which includes a releasably captured compound. Application of energy from source 535 through conduit 540 into the matrix material results in the release of the compound into the flowing fluid 524. The released compound is added to the flowing fluid without appreciably changing the volumetric or mass flow rate of the flowing fluid 524. The mixture 527 of the flowing fluid and compound flows into container 526.

The section of tubing 520 containing the releasably captured compound and the matrix material is the same as catheter assembly 20, except as shown and described differently. The sheath material for tubing 520 does not need to be either biocompatible nor flexible and may be constructed from any material which transmits the energy into the matrix material. The compound releasably captured within the matrix of tubing assembly 520 does not need to be biocompatible or provide therapeutic affect, and may be any material which can be releasably captured within the matrix material and subsequently released by the application of energy to the matrix material. Energy source 535 is the same as energy source 35, except as shown and described differently. Energy source 535 does not need to be biocompatible in terms of the quantity or quality of energy released.

Figure 8:
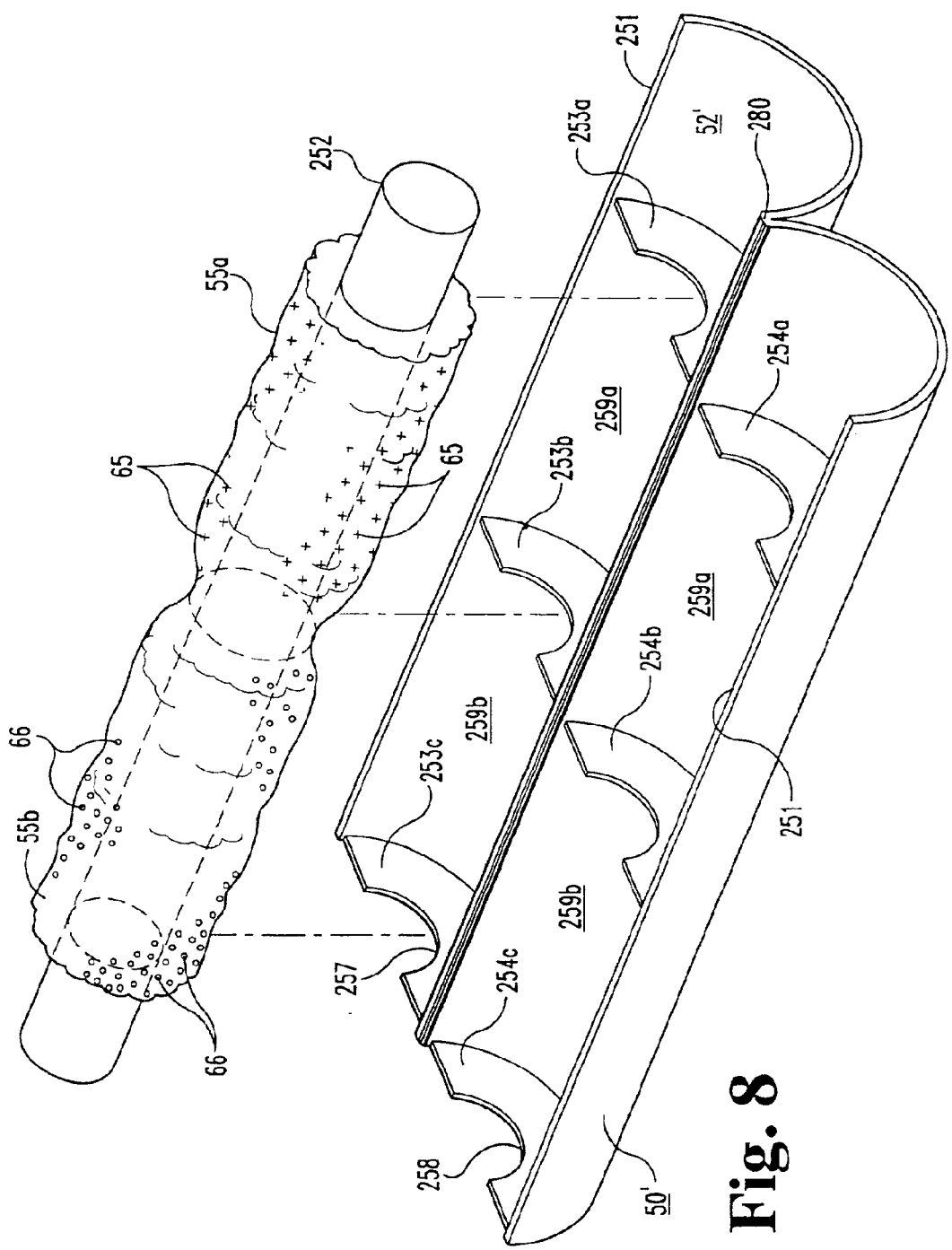
FIG. 8 is a perspective view according to another embodiment of the present invention for manufacturing a catheter assembly.
Figure 9:
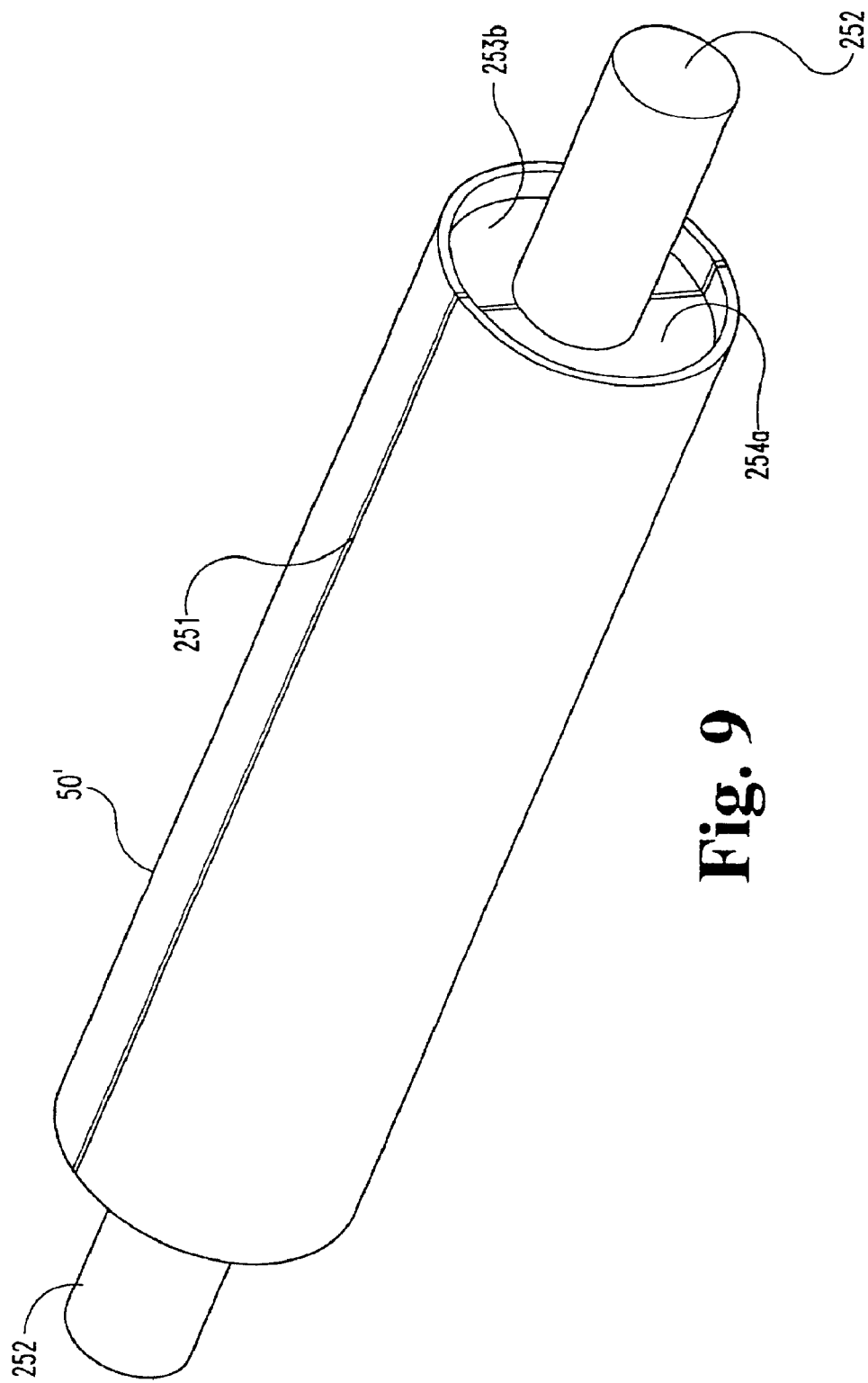
FIG. 9 is a perspective view of the assembly of FIG. 8 with the sheath closed around the rod.

Another embodiment of the present invention relates to a method for manufacturing a catheter assembly. The catheter includes one end that is readily attachable to a laser or non-laser light source. FIGS. 8 and 9 depict a molded outer sheath 50' of laser light conductible fiber optic material and incorporating multiple baffles 253 and 254 to center an inner rod 252 used during assembly of the catheter. Baffles 253 and 254 are semicircular in shape and are integrally molded into sheathing 50'. Each baffle preferably includes a semicircular cutout 257 and 258, respectively. These cutouts are shaped to accept and support a form coated with polymer matrix, such as rod 252 coated with hydrogel 55.

The light carrying section of the outer fiber optic sheath 50 and 50' can be of any thickness that conducts the proper intensity of light. The preferred fiber optic sheath will have a cross sectional area from about 200 to about 3000 microns and preferably about 1200 microns. The choice of the sheath cross sectional area depends on the brightness of the light source and the optical power output required for release of the drug from polymer matrix. In some embodiments, the sheath provides the structural integrity and flexible characteristics of the overall catheter tubing. This material is readily available to one of ordinary skill in the art.

As shown in FIGS. 8 and 9, the catheter sheath 50' is a split cylinder, with the split occurring lengthwise along the sheath. The sheath includes only a single split 251, such that the sheath 50' preferably remains one piece. In some embodiments of the present invention, the molded sheath includes a hinge section 280, such as an area of weakened material, on the side of the sheath opposite the split. This hinged area 280 facilitates a bending apart of the two lengthwise sections of the molded sheath 50'. The two sections can be hinged away from one another so as to facilitate the later insertion of a rod 252 in the central cutout of the baffles.

A biocompatible hydrogel polymer matrix 55 which includes the photolabily bonded therapeutic agent 65 is deposited upon a rod 252 designed to loosely bind the gel material. The rod is composed of a material such as a hard plastic. The surface does not bind tightly to the gel, which may be a property of the hard plastic itself or a property of a rod coating substance such as TEFLON® provided to coat the surface of the rod. The polymer 55 thickness is allowed to build up in the hydrated state around the rod 252 to a thickness such that the volume of the matrix 55 and rod 252 together become greater than the internal volume of the closed catheter sheathing. Various sections of hydrogel material may be included such that each section might incorporate unique compounds or groups of compounds distinct from other sections with regard to their confinement properties and releasing characteristics.

The sheath is formed around the rod-hydrogel section, as seen in FIG. 9. The bent-apart sheath sections are brought back into contact, which may result in a partial squeezing out of some of the hydrogel and therapeutic agent. The lengthwise split 251 is sealed by a method such as adhesion with a bonding agent or ultrasonic welding. The inner surface 52' of the sheath 50', including the baffles 253 and 254, are preferably prepared to accept the hydrogel via adhesive preparation according to U.S. Pat. No. 5,304,121 and designed to accept the hydrogel 55 and affix it to the catheter sheath interior prior to assembly with the rod-gel section.

The assembly is allowed to dry, the subsequent dehydration causing the thickness of the hydrogel to decrease by as much as a factor of 6–10. This substantial reduction in volume permits the hydrogel to pull away from the surface of rod 252, since the adhesion of the hydrogel to the rod surface is less than the adhesion of the hydrogel to the inner surface 52' of the sheathing 50' The rod 252 is then removed, and the sheath is coated on the outer surface with an opaque and reflective coating combination 70 and 75. These coatings can also incorporate a sealer to provide a means to close the seam 251 remaining after the sheath circumscribes the rod-hydrogel section, or a separate step may be needed to close the seam prior to coating. When rehydrated during use the polymer matrix 55 swells and reforms to a shape that allows a lumen 60 to form with a diameter generally determined by the central cutouts of the baffle and the outer diameter of the rod. Appropriate sterile procedures are followed for tubing that is manufactured for parenteral use, such that either suitable sterilization techniques compatible with the catheter materials are followed for components prior to assembly or appropriate post-manufacturing sterilization procedures are carried out, such as radiation bombardment.

Another embodiment of the present invention contemplates a catheter assembly incorporating two different therapeutic agents 65 and 66 which are not mixed within the polymer matrix, and are separated into different sections of the catheter. As best seen in FIG. 8, a portion 55a of the polymer matrix including captured therapeutic agent 65 coats a first portion of rod 252. A portion 55b of the polymer matrix including captured therapeutic agent 66 coats a second portion of rod 252. As coated road 252 is placed within the baffle cutouts, therapeutic agent 65 is largely confined to section 259a of sheath 50', defined between baffles 254a and 254b, and between baffles 253a and 253b. Terapeutic agent 66 is largely confined to section 259b of sheath 50', defined between baffles 254b and 254c, and between baffles 253b and 253c. An arbitrary number and placement of such said sections can be incorporated into the sheath of the present invention. Further, these sheath sections can be supplied by separate laser light pipes capable of transmitting multiple distinct wavelengths of laser energy.

According to another embodiment of the present invention, catheter 20 is manufactured using a split, bent-apart, molded sheath 50'. Sections of a polymer matrix such as 55a and/or 55b are placed within the interior sections 259a or 259b of sheath 50'. A rod 252 which is preferably not coated with a polymer matrix is placed within sheath 50', preferably being supported within the cutouts 257 or 258 of the baffles. The interior surface 52' of sheath 50' is preferably coated as previously described to improve the adhesion of the polymer matrix to surface 52'. Sheath 50' is then formed around rod 252, with split 251 being adhered closed as previously described. The polymer matrix is then shrunk in volume, such as by dehydrating. Rod 252 is removed from the closed sheath. Sheath 50' can include a first section 259a containing a first releaseably captured compound 65, and a second section 259b containing a second releaseably captured compound 66.

According to another embodiment of the present invention, catheter 20 is manufactured using an injection method. A sheath 50 which is not split along its length is preferably supported along the outer diameter of its length in a straight, linear fixture. A rod 252 is held by its ends in the approximate center of the sheath. A quantity of polymer matrix 55a and/or 55b is injected into the annulus between the interior wall 52 of the sheath and the outer diameter of rod 252. The interior surface 52 of sheath 50 is preferably coated as previously described to improve the adhesion of the polymer matrix to surface 52. The polymer matrix is then shrunk in volume, such as by dehydrating. Rod 252 is removed from the sheath.

Figure 5A:
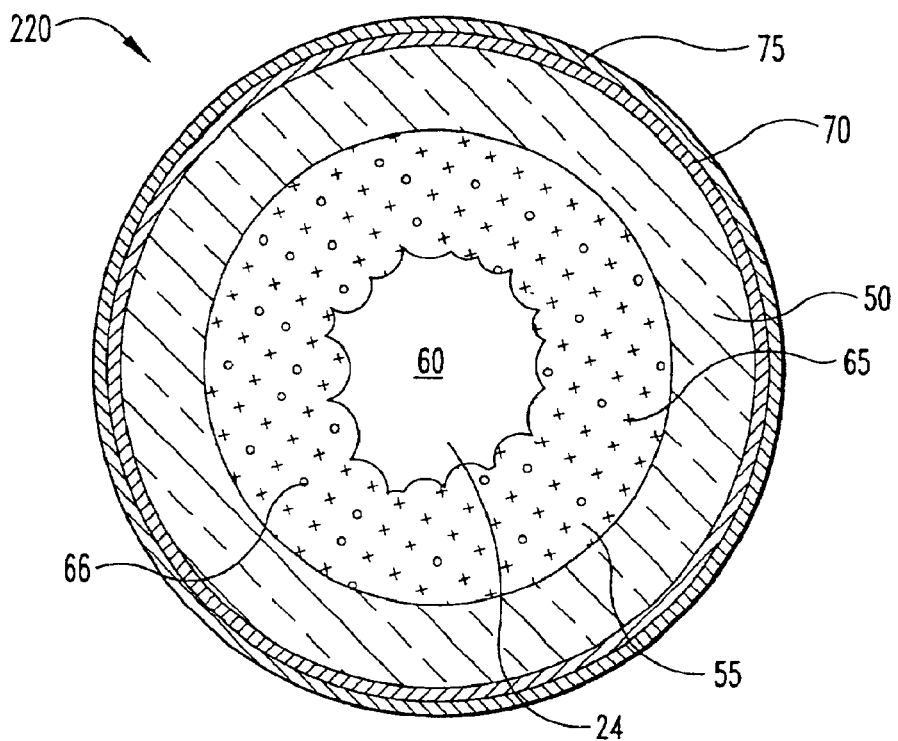
FIG. 5A is a section of a catheter according to another embodiment of the present invention.

In accordance with another embodiment of the present invention, FIG. 5A shows a cross-section of an apparatus 220 which is the same as catheter 20, except as herein described and depicted. In apparatus 220, polymer matrix 55 includes molecules photolabily bonded to two different therapeutic agents 65 and 66. These agents 65 and 66 may represent distinctly different drugs with regard to, but not limited to, such properties as drug pharmacological classification and storage concentration within the catheter body. Further, the laser liable bonds holding drugs 65 and 66 may or may not be characterized by different frequency or intensity of laser liabilities. The use of a coherent laser light source will be preferable in many applications because the use of one or more discrete wavelengths of light energy that can be tuned or adjusted to the particular photolytic reaction occurring in the photolytic linker necessitates only the minimum power (wattage) level necessary to accomplish a desired release of agents such as 65 and 66.

Multiple releases of different therapeutic agents or multiple-step reactions can be accomplished using coherent light of different wavelengths. Intermediate linkages to dye filters may be utilized to screen out or block transmission of light energy at unused or antagonistic wavelengths (particularly cytotoxic or cytogenic wavelengths), and secondary emitters may be utilized to optimize the light energy at the principle wavelength of the laser source. Preferably, light radiation refers to light of wavelengths from about 300 nm to about 1200 nm. This includes UV, visible and infrared light The choice of wavelength will be based on the intended use, namely being selected to match the activation wavelength for the cleavage of the photolabile linkage between the catheter matrix material 55 and compounds 65 and 66 to be released. The art pertaining to the transmission of light energy through fiber optic conduits or other suitable transmission or production means to the remote biophysical site is extensively developed.

This embodiment affords a means of providing selective multi-drug therapies on demand. The present invention also contemplates the storage of multiple drugs within the matrix. For example, drug 65 and drug 66 can be released within the infusate 24 at times which would allow interaction within the infusate prior to release into the systemic circulation.

Figure 5B:
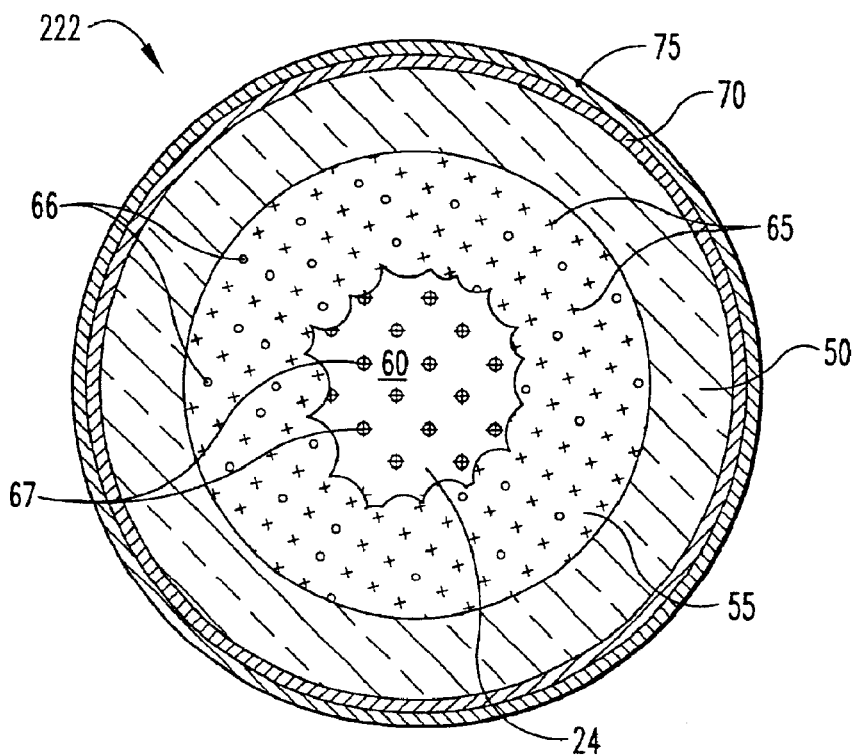
FIG. 5B is a section of a catheter according to another embodiment of the present invention.

In accordance with another embodiment of the present invention, FIG. 5B shows a cross-section of an apparatus 222 which is the same as catheter 20, except as herein described and depicted. In apparatus 222, polymer matrix 55 includes molecules photolabily bonded to two different therapeutic agents 65 and 66. These agents 65 and 66 may represent distinctly different drugs with regard to such properties as drug pharmacological classification and storage concentration within the catheter body. Further, the laser liable bonds holding drugs 65 and 66 may or may not be characterized by different frequency or intensity of laser liabilities. This interaction could result in a prodrug effect, where drug 65 activates or alters drug 66, or drug 65 and drug 66 interact to produce a new drug 67. Then altered drug 66 or drug 67 would be available to the systemic circulation for therapy. This allows for inline synthesis of drugs or compounds that would be otherwise difficult to produce and administer effectively by other means.

The advantages of this device are increased safety to the recipient of infused drug through decreased trauma of infusion site innervations and for maximum maintenance of sterile conditions. Catheters can be used for either short-term or long-term vascular access. Factors associated with infusion-related phlebitis among patients with peripheral venous catheters include site of catheter insertion, experience of personnel inserting the catheter, frequency of dressing change, catheter-related infection, skin preparation, host factors, and emergency-room insertion could all be decreased from use of the present invention. The present invention provides increased safety for general catheter use by providing a drug or other compound to be made immediately available for use when needed for adjunctive therapy without adding any extra equipment into the sterile infusion set environment. This is in contrast to the necessity with current practices for an additional catheter to be inserted, a drug solution to be changed, or any of various other alterations necessary to add adjunctive drug therapy using catheter or tubing system. The present invention provides quick and accurate drug delivery of on-demand doses of new or concurrent multi-drug therapies. The present device can be programmed to release drug at a specified time and in a controlled amount with a degree of accuracy based upon the high degree of accuracy available through computer control of an energy source. The computer control allows administration of a specified and appropriate amount of intensity and duration of energy exposure, preferably coherent light, to the catheter sheath for subsequent release of agents 65 and 66 into infusate solution.

The drug is also released into the catheter lumen which may extend up to and sometimes inside the vasculature setting. A more immediate entrance into a positive flow body cavity space, such as the systemic circulation can be realized with the present device, where drug is stored and released at the opening of a catheter inside the vasculature. This is in contrast to a current adjunctive processes including providing drug into a port which has to travel down the catheter tubing and then enter the systemic circulation. In such cases an attendant is necessary to mix a drug and inject it into the infusion set port, which takes time and adds an element of human error to the process. In some situations a common syringe pump apparatus is in place to administer the adjunctive drug therapy. The present invention has few mechanical parts to fail. The infusion pump apparatus involves many moving parts which increases the risk of malfunction. Both attendant and syringe pump apparatus therapy modifiers inject an added volumetric input to the flow of infusate, thereby limiting their effectiveness if the total flow rate into the biological unit must be limited to a maximum amount. Both adjunctive processes also use a constant concentration of added infusate, so that dynamic changes in dose require dynamic changes in injected infusate volume.

Some embodiments of the present invention incorporate a therapeutic agent 65 with a short half-life into the polymer matrix 55. Because of the short time lag from release of the drug from the matrix into the vasculature of the patient, there is increased effectiveness of the short half-life agent. Examples of these type of drugs would include short acting anesthetic agents such as xylocaine and cardiac agents such as nitrous oxide derivatives, and prostaglandin derivatives. An operator may afford effective feedback control of short acting cardiac drugs, analeptics, neurotransmitters, analgesics, or hormones. During the monitoring of an EKG of a patient in the intensive care unit of a hospital, when arrhythmias are detected or cardiac arrest is indicated, a drug can immediately be released into the systemic circulation for therapy. While monitoring the EEG during anesthesia, drugs can be released into the systemic circulation by the present invention to decrease or increase the depth of anesthesia through proper release of drugs.

The present invention can be used to administer drug in an automatic, easily controlled manner. Traditional drug regimens have included administering drugs orally, sublingually, rectally, subcutaneously, intramuscularly, occularly and parenterally. The regimens with respect to time have included rapid injections, constant rate infusions and combinations thereof. The present invention can be used to administer drug or compound when that drug or compound is administered by a tubing or a catheter system. To deliver any arbitrarily administered drug regimen, a computer controller is programmed to control energy source 35 to administer a defined energy magnitude or duration to the tubing matrix of the present invention so that a proportional amount of stored compound is released into the tubing lumen in a controlled manner. The ease of input profile generation used to control drug release from the present inventions, coupled with their potentially complex characteristics with respect to time represent a very flexible means of drug delivery when traditional methods of drug delivery are considered. A patient can in many instances self-administer the radiation to release drug on an "as required" arbitrary basis, e.g. for hypertension treatment or for pain relief.

Many natural systems exhibit structure characterized by chaotic behavior. Various patterns in nature have been described by fractal geometric curves, surfaces and volumes. There is ample evidence to suggest that many biological systems incorporate chaotic mechanisms in their structure. These chaotic structural mechanisms result in observational data that can be interpreted as fractal in form. Among many biological systems, such systems studied have included cardiac function and neural stimulation.

Figure 13A:
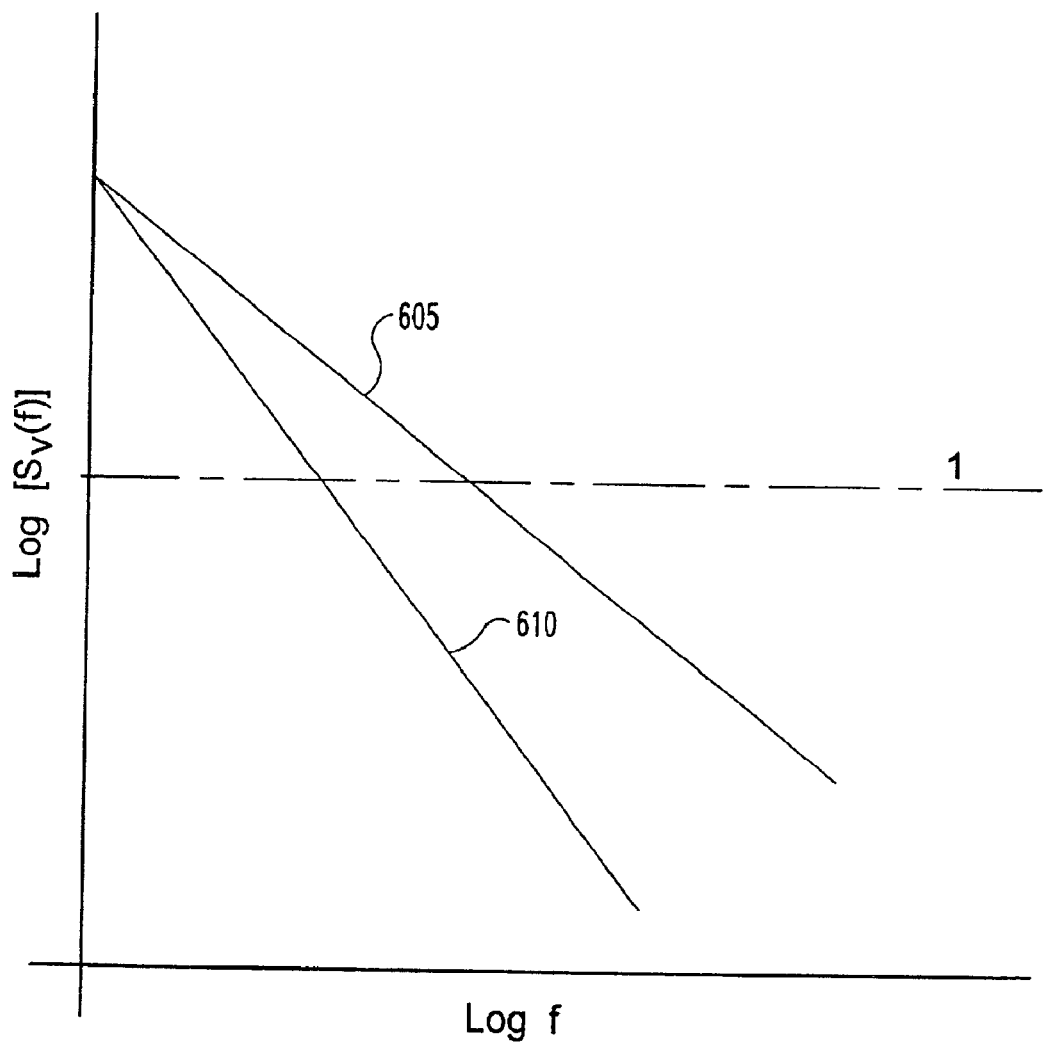
FIG. 13A is a graphical representation of the log of a spectral density verses the log of frequency.

Unpredictable changes over time t of a quantity V is known as noise V(t). The spectral density of V(t), Sv(f), gives an estimate of the mean square fluctuations of the quantity at a frequency f. As seen in FIG. 13A, by plotting log Sv(f) as a function of log f, a slope can be calculated, and this slope can be interpreted as having a functional form $1/f^\beta$, where β is a spectral exponent. Plot 605 of FIG. 13A plots the spectral density of a variable where β is equal to 1. Graph 610 represents the log of the spectral density of a variable for β equal to 2. A particular finding has included the discovery that almost all musical melodies mimic 1/f noise, where 1 is equivalent to "white" noise, and $1/f^2$ corresponds to Brownian motion.

Fractional Brownian motion (fBm) is a mathematical model for many random fractals found in nature, including 1/f noise. Formally, it is the increments of fBm (the differences between successive values) that produce values corresponding to various $1/f^\beta$ noise series. Traces of fBm are characterized by a parameter H in the range of 0<H<1. The value H≈0.8 is empirically a good choice for many natural phenomena. *Fractional* Brownian motion has been studied and various methods of generating trains of 1-, 2- and 3-dimensional data sets have been developed; see: *The Science of Fractal Images*, Eds. Heinz-Otto Petigen and Dietmar Saupe, 1988. These include spatial approximation methods and, approximation by spectral synthesis. These methods can readily be carried out by ordinary computer analysis. According to another embodiment of the present invention, the application of energy to the catheter assembly is applied according to a 1-dimensional algorithm to synthesize fBm *fractional* Brownian motion.

Figure 7:
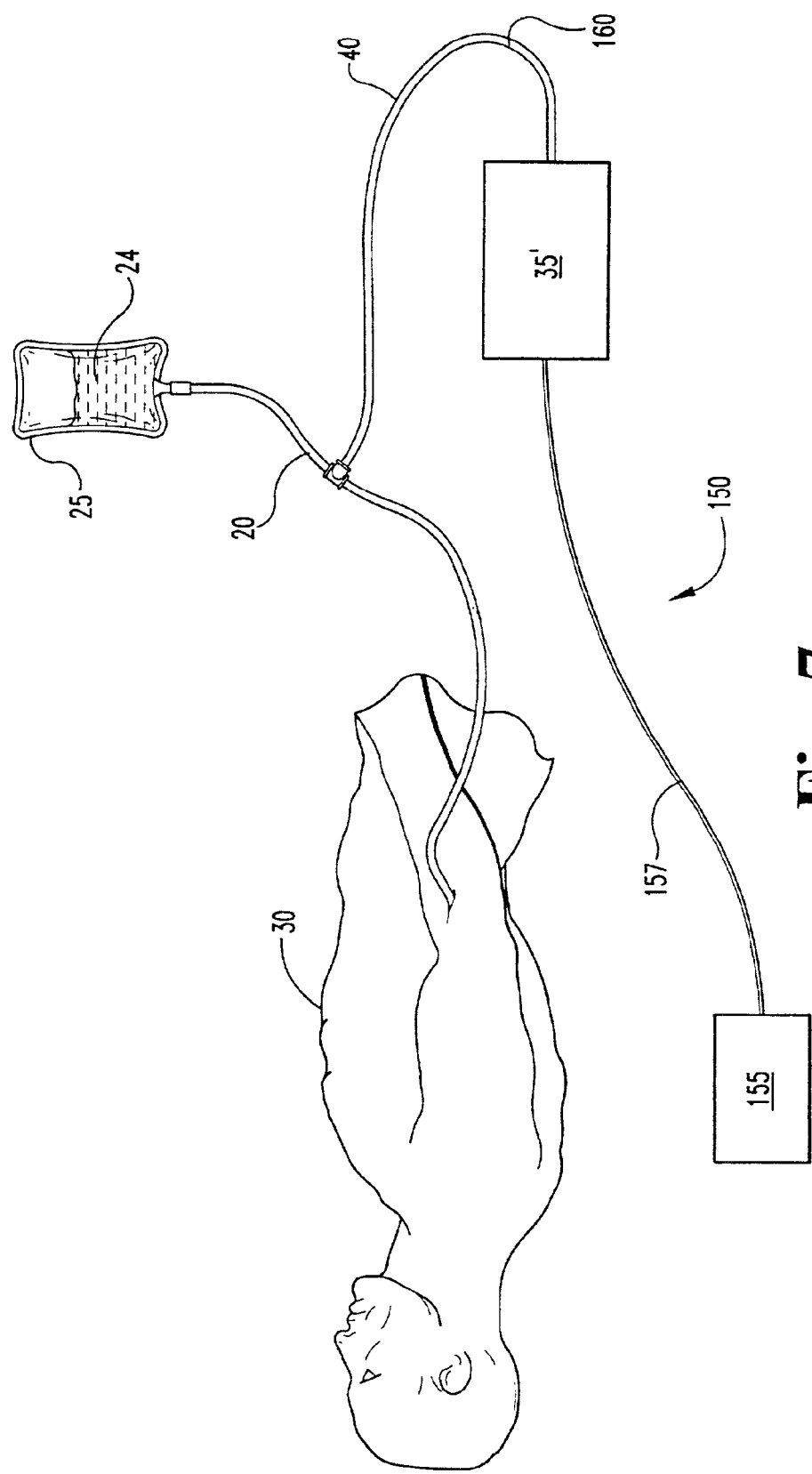
FIG. 7 is a schematic representation according to another embodiment of the present invention for providing a therapeutic agent to a biological unit in a fractally-based pattern.

FIG. 7 schematically depicts a system 150 for delivering therapeutic agent in a fractally-based pulsatile manner to a biological unit 30. An electronic controller 155 produces a fractally derived signal 157 to control an energy source 35', such as a laser. Various methods of generating fBm numerical time series can be used to calculate fractally-based signal 157 by controller 155, such as with Fast Fourier Transform filtering, random midpoint displacement methods, or other methods described in The Science of Fractal Images, Eds. Heinz-Otto Petigen and Dietmar Saupe, 1988. FIG. 13B–D represent three distinct fBm curves $V_f(t)$ synthesized using the midpoint displacement method to produce fBm, where H≈0.8. The fractally derived control signal 157 can also be generated by choosing a value of β, preferably between the values of 0.5 and 1.5. From selection of either H or β, the log of the spectral density of a pulse parameter such as magnitude, duration, and separation interval can be predicted. FIG. 13B, 13C, and 13D represent three distinct fBm curves 620, 630, and 640, respectively, for $V_f(t)$ synthesized using the midpoint displacement method for a selected value of H. Curve 620 of FIG. 13B represents a fractally derived series of laser pulse magnitudes at 6 intervals. FIG. 13C represents a series of fractally derived laser pulse durations at 6 intervals. FIG. 13D represents a series of 6 fractally derived laser pulse spacing intervals. These series have been sampled at regular intervals, $S_i$, to determine the value of the quantity at the particular sampling time. These values are used to assign values to laser pulse parameters. Each pulse is characterized by the parameters of pulse magnitude, $(V_1)$, duration, $(V_2)$ and separation interval, $(V_3)$, from the immediately preceding pulse in the series, $S_p(i)$.

Figure 13E:
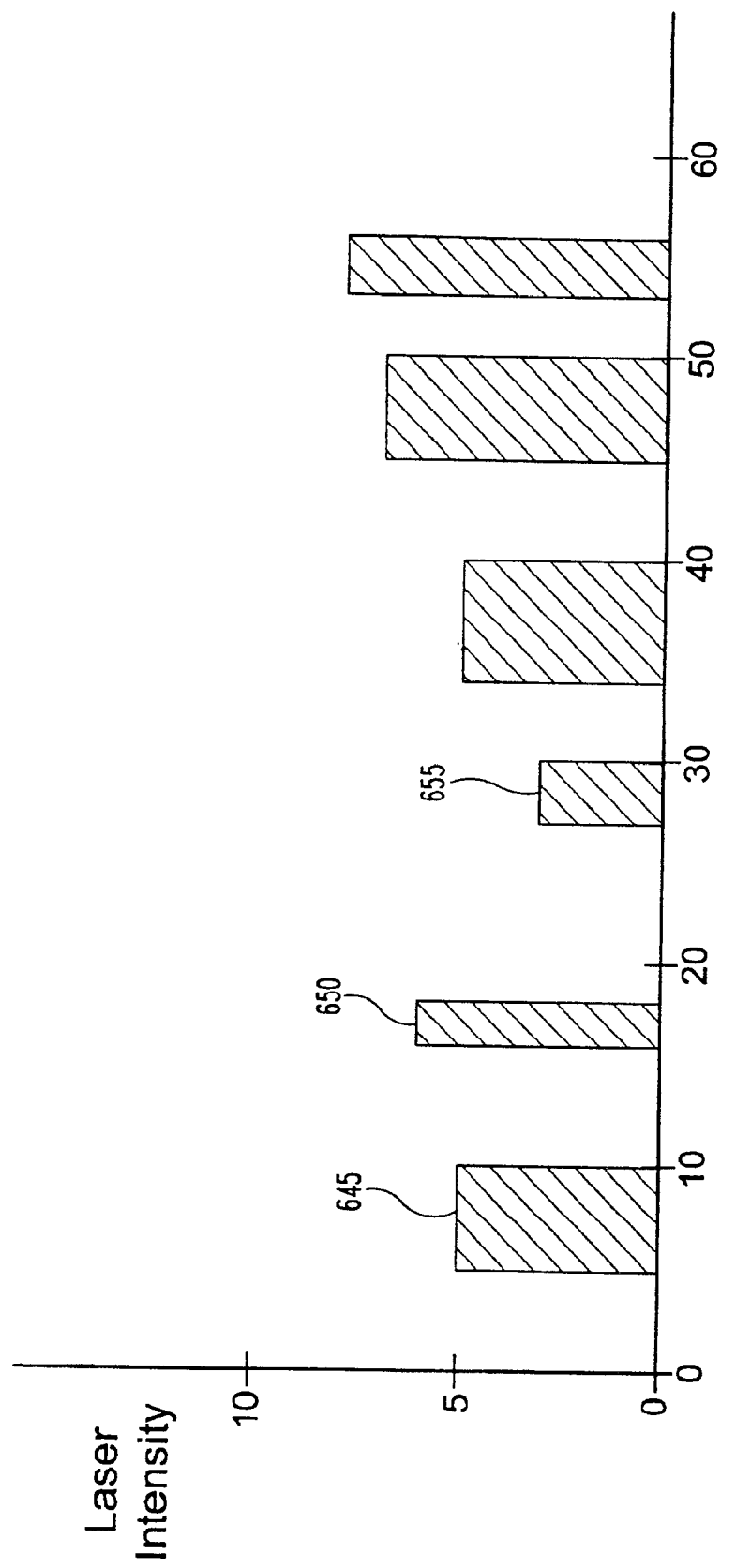
FIG. 13E is a graphical representation of a time history of fractally derived pulses synthesized from the quantities represented in FIGS. 13B, 13C, and 13D.

Numerically, each of these values conforms independently to a fractally-based algorithm for each pulse to produce a fractally derived, time domain pulse train signal, $S_p(i)$, at the series sampling times as shown in FIG. 13E. A time domain pulse train is shown in FIG. 13E, and is synthesized by combining the pulse series of FIG. 13B, 13C, and 13D. As shown in FIG. 13E, there is a first pulse 645 with a magnitude of 5, duration of 5, and an interval spacing of 5 from the origin. A second pulse 650 from sampling interval 2 has a magnitude of 6, a duration of 2, and is spaced 6 units from pulse 645. Pulse 655 has a magnitude of 3, a duration of 3, and is spaced 9 units from pulse 650. The pulse train represented in FIG. 13E represents a model for the laser control signal 157. The pulse train of FIG. 13E is scaled by the appropriate intensity and time factors to take into account the specific embodiment of the invention, considering factors such as the effect of the chosen releasable compound, the volumetric flow rate of the infusate, the rate at which the particular laser breaks the particular photolabile bonds, and other factors. For example, with certain specific therapeutic agents, the time interval shown could be minutes, where as for other specific therapeutic agents the time interval could be hours. As an alternate to the method described above, the present invention contemplates using the difference between successive magnitudes to assign values to pulse parameters. For example of this alternate embodiment, the difference between successive values of FIGS. 13B, 13C, and 13D would be used to generate the time domain pulse train, instead of the values themselves.

Compound fractally-based pulse train signals can be obtained by combining several single pulse series together through superposition and applying this compound pulse series to derive a fractally based signal 157. The signal 157 is provided to energy source 35' to generate a fractally-based stream of energy 160 that enters catheter assembly 20 so as to fracture the bonds between the therapeutic agent and the polymer matrix. These bonds are fractured, and the therapeutic agent is subsequently released in a pulsatile manner. This pulsatile release of therapeutic agent can include predetermined amounts of agent released at variable intervals, variable amounts of therapeutic agents released at predetermined intervals, or variable amounts of therapeutic agent released at variable intervals. Since there is a time lag for the therapeutic agent to defuse out of the polymer matrix and into the infusate flow stream, and further a time lag for the mixture of therapeutic agent and infusate to mix within the biological unit, it is preferable that the frequency content of the pulsed energy 160 be less than about 1 Hz.

Since there is evidence that neuronal systems and cardiac systems exhibit chaotic behavior which can be described in fractal terms, one embodiment of the present invention administers a drug in a pulsatile input train, where the pulse separation and/or pulse magnitude relates to a fractally derived input signal. As one example, the present invention contemplates treatment of an acute cardiac event such as heart arrest or fibrillation in an intensive care ward, where intravenous tubing of the present invention would release a therapeutic agent in a fractally based pattern to the patient in distress. As another example, the present invention contemplates delivery of intravenous anesthesia, where there is an anesthetic response from a fractally based pattern drug delivery. As another example, the present invention contemplates the administration of morphine to a post-operative patient in a fBm pattern. It is anticipated that short acting neurotransmitters or other psychoactive agent may be used in this fashion, such as norepinephrine, epinephrine, and dobutamine.

On a longer time scale, administration of hormones, such as hGH (human growth hormone), can be administered as a fBm pulsatile input to growth deficient patients.

The delivery of drug or compound therapy using routes other than parenteral administration in a fBm profile can also be expected to engender beneficial responses when compared to traditional compound treatment regimens. Traditional dosage forms which could incorporate these fractally-based timed release regimens of drug release include, but are not limited to, intramuscular matrix embedded depot, subcutaneous depot injections and various suppository preparations.

Input stimulus other than chemical modifiers when administered as fBm regimens, for example through pulsatile light stimulation to the eye or other non-drug means, may elicit a potentiated or a muted evoked response when compared to a steady application of an effector stimuli. Such fBm treatment may include cancer radiation treatments, audible stimulation or any other stimuli sensed by a living system. The frequency content of the pulsed energy can be greater or less than 1 Hz.

It is contemplated that the various embodiments described heretofore are combinable. For example, the release of compound in a fractally-based pattern can be incorporated into system 500.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A catheter for delivering fluid, comprising:
   a flexible outer sheath having an interior surface and an exterior surface;
   a polymer matrix attached to the interior surface of said sheath, said polymer matrix defining a lumen therethrough for flow of the liquid;
   a therapeutic agent releasably captured by the molecules of said polymer matrix
   a source of energy for releasing said therapeutic agent from said polymer matrix;
   a controller operably coupled to said source of energy; and
   a sensor for sensing a response and producing a signal related thereto,
   wherein said controller activates said energy source in response to said signal.

2. The catheter of claim 1 wherein said therapeutic agent is releasably captured by covalent bonding molecules of said agent to molecules of said polymer matrix.

3. The catheter of claim 1 wherein said polymer matrix is a hydrogel.

4. The catheter of claim 1 which further comprises a source of energy for releasing said therapeutic agent from said polymer matrix.

5. The catheter of claim 4 wherein said source is a laser and said outer sheath transmits energy from said laser into said polymer matrix.

6. The catheter of claim 5 wherein said source is a laser irradiating the polymer matrix with laser pulses of varying time duration.

7. The catheter of claim 5 wherein said source is a laser irradiating the polymer matrix with laser pulses of varying radiation intensity.

8. The catheter of claim 5 which further comprises a fiber optic cable for optically coupling said laser to said sheath.

9. The catheter of claim 1 which further comprises a source of infusate liquid for flowing liquid through said lumen, wherein the therapeutic agent released by said source of energy diffuses through said polymer matrix and into said infusate liquid.

10. The catheter of claim 1 wherein said therapeutic agent is a first therapeutic agent, and which further comprises a second therapeutic agent intermixed in said polymer matrix with said first therapeutic agent, said second therapeutic agent being releasably captured by the molecules of said polymer matrix.

11. The catheter of claim 1 wherein said controller includes a cardiac monitor and said sensor responds to cardiac activity.

12. The catheter of claim 1 wherein said controller operating said source of energy to provide energy to said polymer matrix in a fractally-based pattern.

13. The catheter of claim 1 wherein said outer sheath includes a first interior section and a second interior section, and which further comprises a baffle separating said first section from said second section, said first section and said second section each including a portion of polymer matrix, and which further comprises a first therapeutic agent releasably captured in said polymer matrix of said first section and a second therapeutic agent releasably captured in said polymer matrix of said second section.

14. The catheter of claim 1 wherein said outer sheath includes an opaque coating on the exterior surface for limiting the escape of radiation from said outer sheath.

15. The catheter of claim 1 wherein said outer sheath includes a reflective coating on the exterior surface for reflecting radiation into said polymer matrix.

* * * * *